(12) United States Patent
Wieslander et al.

(10) Patent No.: US 11,718,546 B2
(45) Date of Patent: Aug. 8, 2023

(54) SYSTEM AND A METHOD FOR PRODUCING MICROBIOLOGICALLY CONTROLLED FLUID

(71) Applicants: BAXTER INTERNATIONAL INC., Deerfield, IL (US); BAXTER HEALTHCARE SA, Glattpark (CH)

(72) Inventors: Anders Wieslander, Lund (SE); Olof Jansson, Vellinge (SE); Per-Ola Wictor, Stehag (SE); Anders Wellings, Bellair Beach, FL (US); Helena Jeppsson, Horby (SE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 754 days.

(21) Appl. No.: 16/610,384

(22) PCT Filed: Nov. 6, 2017

(86) PCT No.: PCT/EP2017/078347
§ 371 (c)(1),
(2) Date: Nov. 1, 2019

(87) PCT Pub. No.: WO2018/202321
PCT Pub. Date: Nov. 8, 2018

(65) Prior Publication Data
US 2020/0069858 A1 Mar. 5, 2020
US 2023/0202896 A9 Jun. 29, 2023

Related U.S. Application Data

(63) Continuation of application No. 15/588,454, filed on May 5, 2017, now Pat. No. 10,828,412, which is a
(Continued)

(30) Foreign Application Priority Data

Jun. 15, 2017 (SE) .................................. 1750759-1

(51) Int. Cl.
*C02F 9/00* (2006.01)
*A61M 1/16* (2006.01)
(Continued)

(52) U.S. Cl.
CPC ............. *C02F 9/00* (2013.01); *A61M 1/1605* (2014.02); *A61M 1/166* (2014.02);
(Continued)

(58) Field of Classification Search
USPC ....................................................... 210/322
See application file for complete search history.

(56) References Cited

U.S. PATENT DOCUMENTS 3,563,381 A 2/1971 Edelson et al.
3,685,680 A 8/1972 Tenckhoff et al.
(Continued)

FOREIGN PATENT DOCUMENTS

EP 0171550 2/1986
EP 0749328 12/1996
(Continued)

OTHER PUBLICATIONS

International Search Report for corresponding International Application PCT/US2009/031809 dated Oct. 19, 2009.
(Continued)

*Primary Examiner* — Patrick Orme
(74) *Attorney, Agent, or Firm* — K&L Gates LLP

(57) ABSTRACT

A method and a system comprising an integrated water purifying apparatus with a pre-filter circuit including a particle filter and an activated carbon filter arranged to produce pre-treated water; a fluid circuit arranged to receive pre-treated water from the pre-filter circuit, the fluid circuit including an RO-pump and a Reverse Osmosis (RO) device arranged to produce purified water; a heating device arranged to heat purified water from the RO device to a
(Continued)

temperature above 65°0 C.; the water purifying apparatus further arranged to heat disinfect the fluid circuit using the heated purified water. The system further comprises a line set connected to the purified water outlet connector at a water line connector of the line set, wherein the line set includes at least one sterile sterilizing grade filter arranged to further filter the purified water.

20 Claims, 6 Drawing Sheets

Related U.S. Application Data continuation of application No. PCT/US2017/031405, filed on May 5, 2017.

(60) Provisional application No. 62/332,617, filed on May 6, 2016, provisional application No. 62/332,623, filed on May 6, 2016, provisional application No. 62/332,630, filed on May 6, 2016.

(51) Int. Cl.
*C02F 1/02* (2006.01)
*A61M 1/28* (2006.01)
*C02F 1/44* (2023.01)
*C02F 1/00* (2023.01)
*C02F 103/02* (2006.01)

(52) U.S. Cl.
CPC ........ *A61M 1/1656* (2013.01); *A61M 1/1666* (2014.02); *A61M 1/28* (2013.01); *A61M 1/281* (2014.02); *A61M 1/282* (2014.02); *A61M 1/284* (2014.02); *A61M 1/287* (2013.01); *C02F 1/008* (2013.01); *C02F 1/02* (2013.01); *C02F 1/441* (2013.01); *C02F 1/444* (2013.01); *A61M 2205/12* (2013.01); *A61M 2205/18* (2013.01); *A61M 2205/3317* (2013.01); *A61M 2205/3331* (2013.01); *A61M 2205/3337* (2013.01); *A61M 2205/3368* (2013.01); *A61M 2205/3569* (2013.01); *A61M 2205/36* (2013.01); *A61M 2205/3653* (2013.01); *A61M 2205/50* (2013.01); *A61M 2205/502* (2013.01); *A61M 2205/6054* (2013.01); *A61M 2205/6072* (2013.01); *A61M 2205/702* (2013.01); *A61M 2205/705* (2013.01); *A61M 2205/75* (2013.01); *A61M 2205/7518* (2013.01); *C02F 2103/026* (2013.01); *C02F 2209/03* (2013.01); *C02F 2209/40* (2013.01)

(56) References Cited

U.S. PATENT DOCUMENTS

| | | |
|---|---|---|
| 3,744,636 A | 7/1973 | Commarmot |
| 3,814,249 A | 6/1974 | Eaton |
| 3,878,095 A | 4/1975 | Frasier et al. |
| 3,915,802 A | 10/1975 | Kominek |
| 4,060,485 A | 11/1977 | Eaton |
| 4,067,803 A | 1/1978 | Quentin |
| 4,209,402 A | 6/1980 | Gentles |
| 4,348,280 A | 9/1982 | George et al. |
| 4,360,323 A | 11/1982 | Anderson |
| 4,655,941 A | 4/1987 | Suzuki |
| 4,664,891 A | 5/1987 | Cosentino et al. |
| 4,734,198 A | 3/1988 | Harm et al. |
| 4,955,508 A | 9/1990 | Capanna et al. |
| 4,976,683 A | 12/1990 | Gauthier et al. |
| 5,032,265 A | 7/1991 | Jha et al. |
| 5,122,516 A | 6/1992 | Watanabe et al. |
| 5,236,476 A | 8/1993 | Klick |
| 5,256,371 A | 10/1993 | Pippert |
| 5,259,954 A | 11/1993 | Taylor |
| 5,274,434 A | 12/1993 | Morioka et al. |
| 5,295,505 A | 3/1994 | Polaschegg et al. |
| 5,318,750 A | 6/1994 | Lascombes |
| 5,326,473 A | 7/1994 | Lascombes et al. |
| 5,385,564 A | 1/1995 | Slater et al. |
| 5,498,338 A * | 3/1996 | Kruger .................. A61M 1/284 210/259 |
| 5,540,842 A | 7/1996 | Aoyama et al. |
| 5,591,344 A | 1/1997 | Kenley et al. |
| 5,616,248 A | 4/1997 | Schal |
| 5,658,456 A | 8/1997 | Kenley et al. |
| 5,866,880 A | 2/1999 | Seitz et al. |
| 5,895,578 A | 4/1999 | Simard et al. |
| 5,906,978 A | 5/1999 | Ash |
| 5,945,449 A | 8/1999 | Purcell et al. |
| 5,948,251 A | 9/1999 | Brugger |
| 5,954,958 A | 9/1999 | Folden |
| 6,146,536 A | 11/2000 | Twardowski |
| 6,210,803 B1 | 4/2001 | Backhaus et al. |
| 6,228,047 B1 | 5/2001 | Dadson |
| 6,251,279 B1 | 6/2001 | Peterson et al. |
| 6,254,567 B1 | 7/2001 | Tau et al. |
| 6,274,103 B1 | 8/2001 | Taylor |
| 6,277,815 B1 | 8/2001 | Knerr |
| 6,280,634 B1 | 8/2001 | Shah et al. |
| 6,348,162 B1 | 2/2002 | Ash |
| 6,361,201 B1 | 3/2002 | Russell et al. |
| 6,364,143 B1 | 4/2002 | Knierbein |
| 6,419,825 B1 | 7/2002 | Hahmann et al. |
| 6,426,056 B2 | 7/2002 | Taylor |
| 6,429,294 B1 | 8/2002 | Masuda et al. |
| 6,464,977 B2 | 10/2002 | Kai et al. |
| 6,485,479 B1 | 11/2002 | Knierbein |
| 6,489,301 B1 | 12/2002 | Kobira et al. |
| 6,572,641 B2 | 6/2003 | Brugger et al. |
| 6,582,385 B2 | 6/2003 | Burbank et al. |
| 6,595,944 B2 | 7/2003 | Balschat et al. |
| 6,623,709 B2 | 9/2003 | Taylor |
| 6,635,179 B1 | 10/2003 | Summerton et al. |
| 6,645,191 B1 | 11/2003 | Knerr et al. |
| 6,656,355 B2 | 12/2003 | Sano |
| 6,673,376 B1 | 1/2004 | Knerr et al. |
| 6,685,831 B2 | 2/2004 | Donig et al. |
| 6,689,393 B1 | 2/2004 | Knerr |
| 6,745,903 B2 | 6/2004 | Grandics |
| 6,749,818 B2 | 6/2004 | Sano et al. |
| 6,752,928 B2 | 6/2004 | Pfeil et al. |
| 6,758,975 B2 | 7/2004 | Peabody et al. |
| 6,787,032 B2 | 9/2004 | Kurome et al. |
| 6,796,971 B2 | 9/2004 | Anderson et al. |
| 6,814,869 B2 | 11/2004 | Brandl et al. |
| 6,861,033 B2 | 3/2005 | Mullins et al. |
| 6,890,157 B2 | 5/2005 | Pfeil et al. |
| 6,902,670 B2 | 6/2005 | Ho |
| 6,908,546 B2 | 6/2005 | Smith |
| 6,923,987 B2 | 8/2005 | Kai et al. |
| 6,986,872 B2 | 1/2006 | Taylor |
| 7,029,456 B2 | 4/2006 | Ware et al. |
| 7,045,061 B2 | 5/2006 | Nishimura et al. |
| 7,077,956 B2 | 7/2006 | Rovatti |
| 7,108,790 B2 | 9/2006 | Collins et al. |
| 7,208,092 B2 | 4/2007 | Micheli |
| 7,250,619 B2 | 7/2007 | Taylor et al. |
| 7,290,680 B2 | 11/2007 | Henry et al. |
| 7,300,674 B2 | 11/2007 | Tobe |
| 7,311,886 B2 | 12/2007 | D'Ayot et al. |
| 7,345,029 B2 | 3/2008 | Zimmeck |
| 7,419,587 B2 | 9/2008 | Valbjoern et al. |
| 7,419,597 B2 | 9/2008 | Brugger et al. |
| 7,544,300 B2 | 6/2009 | Brugger et al. |
| 7,550,446 B2 | 6/2009 | Henning |
| 7,563,244 B2 | 7/2009 | Kent et al. |
| 7,699,806 B2 | 4/2010 | Ware et al. |
| 7,749,393 B2 | 7/2010 | Brugger et al. |
| 7,758,082 B2 | 7/2010 | Weigel et al. |
| 7,790,043 B2 | 9/2010 | Brugger et al. |
| 7,798,997 B2 | 9/2010 | Kamen et al. |

(56) References Cited

U.S. PATENT DOCUMENTS

| | | |
|---|---|---|
| 7,828,786 B2 | 11/2010 | Ramella |
| 7,837,666 B2 | 11/2010 | Jensen et al. |
| 7,857,802 B2 | 12/2010 | Bradenburger et al. |
| 7,875,015 B2 | 1/2011 | Pahlberg et al. |
| 7,875,016 B2 | 1/2011 | Paulberg et al. |
| 7,892,423 B2 | 2/2011 | Rohde et al. |
| 7,976,711 B2 | 7/2011 | Brugger et al. |
| 7,985,212 B2 | 7/2011 | Jensen et al. |
| 8,052,631 B2 | 8/2011 | Jensen et al. |
| 8,071,055 B2 | 12/2011 | Newcombe |
| 8,128,611 B2 | 3/2012 | Watts et al. |
| 8,162,915 B2 | 4/2012 | Brandenburger et al. |
| 8,177,977 B2 * | 5/2012 | Gaignet ............... C02F 9/005 210/600 |
| 8,192,387 B2 | 6/2012 | Brugger et al. |
| 8,202,420 B2 | 6/2012 | Brugger et al. |
| 8,216,452 B2 | 7/2012 | Rohde et al. |
| 8,246,826 B2 | 8/2012 | Wilt et al. |
| 8,251,971 B2 | 8/2012 | Graf et al. |
| 8,317,750 B2 | 11/2012 | Ware et al. |
| 8,328,784 B2 | 12/2012 | Jensen et al. |
| 8,354,029 B2 | 1/2013 | Hank |
| 8,357,298 B2 | 1/2013 | Demers et al. |
| 8,409,441 B2 | 4/2013 | Wilt et al. |
| 8,409,445 B2 | 4/2013 | Levin et al. |
| 8,425,767 B2 | 4/2013 | Fava et al. |
| 8,460,228 B2 | 6/2013 | Burbank et al. |
| 8,460,558 B2 | 6/2013 | Brugger et al. |
| 8,469,331 B2 | 6/2013 | Burbank et al. |
| 8,496,824 B2 | 7/2013 | Remkes et al. |
| 8,501,009 B2 | 8/2013 | Peterson et al. |
| 8,517,597 B2 | 8/2013 | Shreve |
| 8,524,086 B2 | 9/2013 | Peterson et al. |
| 8,529,766 B2 | 9/2013 | Minami et al. |
| 8,540,875 B2 | 9/2013 | Levin et al. |
| 8,545,428 B2 | 10/2013 | Burbank et al. |
| 8,585,681 B2 | 11/2013 | Boenig et al. |
| 8,585,907 B2 | 11/2013 | Raiford et al. |
| 8,597,223 B2 | 12/2013 | Dumon D'Ayot et al. |
| 8,617,134 B2 | 12/2013 | Brehm et al. |
| 8,617,393 B2 | 12/2013 | Remkes et al. |
| 8,622,986 B2 | 1/2014 | Ramella et al. |
| 8,671,996 B2 | 3/2014 | Weilhoefer et al. |
| 8,673,139 B2 * | 3/2014 | Hedmann ............ A61M 1/166 210/90 |
| 8,678,224 B2 | 3/2014 | Dumont D'Ayot et al. |
| 8,679,348 B2 | 3/2014 | Burbank et al. |
| 8,685,251 B2 | 4/2014 | Smejtek et al. |
| 8,715,214 B2 | 5/2014 | Kopperschmidt |
| 8,758,626 B2 * | 6/2014 | Wong ............... C02F 1/281 210/488 |
| 8,771,749 B2 | 7/2014 | Oda et al. |
| 8,791,078 B2 | 7/2014 | Kirschner |
| 8,813,769 B2 | 8/2014 | Gastaur et al. |
| 8,821,719 B2 | 9/2014 | Becker |
| 8,870,811 B2 * | 10/2014 | Gavin ............... A61M 1/287 604/131 |
| 8,882,737 B2 | 11/2014 | Grap et al. |
| 8,906,240 B2 | 12/2014 | Crnkovich et al. |
| 8,961,872 B2 | 2/2015 | Fehr et al. |
| 9,005,150 B2 | 4/2015 | Ware et al. |
| 9,011,765 B2 | 4/2015 | Rahn et al. |
| 9,022,765 B2 | 4/2015 | Rahn et al. |
| 9,084,855 B2 | 7/2015 | Ware et al. |
| 9,095,499 B2 | 8/2015 | Kugelmann et al. |
| 9,132,220 B2 | 9/2015 | Kugelmann et al. |
| 9,138,526 B2 | 9/2015 | Ware et al. |
| 9,155,824 B2 | 10/2015 | Eyrard et al. |
| 9,180,069 B2 | 11/2015 | Jensen et al. |
| 9,220,800 B2 | 12/2015 | Shenberg |
| 9,220,828 B2 | 12/2015 | Coates |
| 9,249,345 B2 | 2/2016 | Schweitzer et al. |
| 9,265,874 B2 | 2/2016 | Kloeffel |
| 9,274,073 B2 | 3/2016 | Nier et al. |
| 9,314,742 B2 * | 4/2016 | Goodfellow ........ B01D 61/022 |
| 9,328,969 B2 * | 5/2016 | Wrazel ................ C02F 9/005 |
| 9,375,524 B2 * | 6/2016 | Levin ............... A61M 1/1666 |
| 9,388,059 B2 | 7/2016 | Burbank et al. |
| 9,399,089 B2 | 7/2016 | Nikolic et al. |
| 9,440,017 B2 * | 9/2016 | Rohde ............... A61M 1/1605 |
| 10,716,886 B2 * | 7/2020 | Wieslander ........ A61M 1/1605 |
| 2003/0135250 A1 | 7/2003 | Lauman et al. |
| 2003/0220605 A1 | 11/2003 | Bowman et al. |
| 2005/0008505 A1 | 1/2005 | Capp et al. |
| 2005/0139530 A1 * | 6/2005 | Heiss ................ C02F 9/00 210/257.2 |
| 2007/0163965 A1 | 7/2007 | Wolfe |
| 2007/0237835 A1 | 10/2007 | Passlick-Deetjen et al. |
| 2007/0278155 A1 | 12/2007 | Lo et al. |
| 2008/0045877 A1 | 2/2008 | Levin et al. |
| 2008/0058697 A1 | 3/2008 | Kamen |
| 2008/0203023 A1 | 8/2008 | Burbank et al. |
| 2008/0210606 A1 | 9/2008 | Burbank |
| 2008/0230450 A1 * | 9/2008 | Burbank ............ A61M 1/1672 210/85 |
| 2009/0008318 A1 | 1/2009 | Anes et al. |
| 2009/0008331 A1 | 1/2009 | Wilt et al. |
| 2009/0012460 A1 | 1/2009 | Steck et al. |
| 2009/0012655 A1 | 1/2009 | Kienman et al. |
| 2009/0045121 A1 | 2/2009 | Kabayama et al. |
| 2009/0182263 A1 * | 7/2009 | Burbank ............ A61M 1/3413 210/767 |
| 2009/0218285 A1 | 9/2009 | Hank |
| 2010/0018923 A1 | 1/2010 | Rohde et al. |
| 2010/0051546 A1 | 3/2010 | Vuong et al. |
| 2010/0078002 A1 | 4/2010 | Weilhoefer et al. |
| 2010/0137693 A1 | 6/2010 | Porras et al. |
| 2010/0266742 A1 * | 10/2010 | Ferreira ............ B67D 1/0888 426/477 |
| 2010/0326916 A1 | 12/2010 | Wrazel et al. |
| 2010/0332149 A1 | 12/2010 | Scholpp |
| 2011/0100913 A1 | 5/2011 | Minami et al. |
| 2011/0180480 A1 | 7/2011 | Kloeffel et al. |
| 2011/0186521 A1 | 8/2011 | Burbank et al. |
| 2011/0192796 A1 | 8/2011 | Smejtek et al. |
| 2011/0315611 A1 | 12/2011 | Fulkerson et al. |
| 2012/0074060 A1 | 3/2012 | Lass |
| 2012/0095392 A1 * | 4/2012 | Jensen ............... A61J 1/2089 604/29 |
| 2012/0138533 A1 | 6/2012 | Curtis et al. |
| 2012/0310150 A1 | 6/2012 | Brandl et al. |
| 2012/0199205 A1 | 8/2012 | Eyrard et al. |
| 2013/0004593 A1 | 1/2013 | Kloeffel et al. |
| 2013/0008854 A1 | 1/2013 | Wallace et al. |
| 2013/0020237 A1 | 1/2013 | Wilt et al. |
| 2013/0062265 A1 | 3/2013 | Balschat et al. |
| 2013/0105025 A1 | 5/2013 | Fehr et al. |
| 2013/0195717 A1 | 8/2013 | Fehr et al. |
| 2013/0228505 A1 | 9/2013 | Burbank et al. |
| 2013/0240441 A1 | 9/2013 | Terpin et al. |
| 2013/0333795 A1 | 12/2013 | Balschat et al. |
| 2014/0018727 A1 * | 1/2014 | Burbank ............ A61M 1/1672 604/28 |
| 2014/0034657 A1 | 2/2014 | Eyrard et al. |
| 2014/0076058 A1 | 3/2014 | Brugger et al. |
| 2014/0091022 A1 | 4/2014 | Raiford et al. |
| 2014/0144794 A1 | 5/2014 | Eyrard et al. |
| 2014/0191501 A1 | 7/2014 | Brugger et al. |
| 2014/0209520 A1 | 7/2014 | Koch et al. |
| 2014/0220699 A1 | 8/2014 | Pudil et al. |
| 2014/0224737 A1 | 8/2014 | Fichert et al. |
| 2014/0230923 A1 | 8/2014 | Brehm et al. |
| 2014/0238912 A1 | 8/2014 | Vincent |
| 2014/0316332 A1 | 10/2014 | Lo et al. |
| 2015/0005699 A1 * | 1/2015 | Burbank ............ A61M 1/282 604/29 |
| 2015/0008183 A1 * | 1/2015 | Crnkovich ........ A61M 1/1607 210/646 |
| 2015/0041377 A1 * | 2/2015 | Heyes ................ A61M 1/1672 210/321.67 |
| 2016/0038522 A1 | 2/2016 | Carlson et al. |
| 2016/0058933 A1 | 3/2016 | Ballantyne et al. |
| 2016/0101227 A1 | 4/2016 | Norris et al. |

(56) References Cited

U.S. PATENT DOCUMENTS

| | | | |
|---|---|---|---|
| 2016/0213832 A1 | 7/2016 | Eyrard et al. | |
| 2016/0340214 A1* | 11/2016 | Turk | C02F 1/32 |
| 2017/0001887 A1 | 1/2017 | Weigel et al. | |
| 2017/0182237 A1 | 6/2017 | Burbank et al. | |
| 2017/0203022 A1 | 7/2017 | Burbank et al. | |
| 2017/0203024 A1 | 7/2017 | Burbank et al. | |
| 2017/0203025 A1 | 7/2017 | Burbank et al. | |
| 2017/0203026 A1 | 7/2017 | Burbank et al. | |
| 2017/0203027 A1 | 7/2017 | Burbank et al. | |
| 2020/0122087 A1* | 4/2020 | Jansson | C02F 1/441 |
| 2020/0129927 A1* | 4/2020 | Sendelius | A61M 1/1656 |
| 2021/0363030 A1* | 11/2021 | Wictor | C02F 1/441 |

FOREIGN PATENT DOCUMENTS

| | | | |
|---|---|---|---|
| EP | 1614437 | 1/2006 | |
| EP | 2180908 | 5/2010 | |
| EP | 2181965 | 5/2010 | |
| EP | 2190552 | 6/2010 | |
| EP | 1349632 | 2/2011 | |
| EP | 1765254 | 2/2012 | |
| EP | 2501357 | 4/2014 | |
| EP | 2765971 | 8/2014 | |
| EP | 2569028 | 9/2015 | |
| EP | 2670373 | 2/2016 | |
| EP | 2387422 | 10/2016 | |
| WO | 1992018048 | 10/1992 | |
| WO | 9625214 | 8/1996 | |
| WO | 96/40318 | 12/1996 | |
| WO | 9906082 | 2/1999 | |
| WO | 2006005391 | 1/2006 | |
| WO | WO-2008105580 A1 * | 9/2008 | B01D 61/025 |
| WO | 2008-138311 | 11/2008 | |
| WO | 2008138311 | 11/2008 | |
| WO | WO/2009/025545 | 2/2009 | |
| WO | WO2010081672 | 7/2010 | |
| WO | 2011/069110 | 6/2011 | |
| WO | 2011101428 | 8/2011 | |
| WO | 2011/141186 | 11/2011 | |
| WO | WO/2012/104405 | 8/2012 | |
| WO | 2013/055283 | 4/2013 | |
| WO | 2013141896 | 9/2013 | |
| WO | 2013/173349 | 11/2013 | |
| WO | 2016057982 | 4/2016 | |

OTHER PUBLICATIONS

Written Opinion for corresponding International Application PCT/US2009/031809 dated Oct. 19, 2009.
U.S. Appl. No. 60/903,582, filed Feb. 27, 2007.
U.S. Appl. No. 60/904,024, filed Feb. 27, 2007.
U.S. Appl. No. 61/092,239, filed Aug. 27, 2008.
U.S. Appl. No. 61/489,544, filed May 24, 2011.
U.S. Appl. No. 61/498,394, filed Jun. 17, 2011.
U.S. Appl. No. 62/003,374, filed May 27, 2014.
U.S. Appl. No. 62/004,567, filed May 29, 2014.
Search Report Issued in French application No. 1452117, dated Mar. 31, 2016, 2 pages.
Written Opinion Issued in French application No. 1452117, dated Mar. 31, 2016, 5 pages.
European Communication dated Mar. 20, 2015 for Application No. 09 710 209.9-1662, 6 pages.
Search and Examination Report dated Jul. 29, 2014 for related GB Appl. No. 1322331.8.
Office Action for Mexican Patent Application No. Mx/a/2010/008961 dated Jul. 1, 2013.
Manns et al., "The acu-menTM: A new device for continuous renal replacement therapy in acute renal failure", Kidney International, 1998, pp. 268-274, vol. 54.
European Search Report dated Mar. 21, 2017—Appl. 16176496.4-1664 (10 pages).
International Search Report and Written Opinion dated Sep. 26, 2017 issued in corresponding PCT Application.

\* cited by examiner

SYSTEM AND A METHOD FOR PRODUCING MICROBIOLOGICALLY CONTROLLED FLUID

PRIORITY CLAIM

The present application is a National Phase of International Application No. PCT/EP2017/078347, filed Nov. 6, 2017, which claims priority to (i) U.S. patent application Ser. No. 15/588,454, filed May 5, 2017 (ii) International Application No. PCT/US2017/031405, filed May 5, 2017, and (iii) Swedish Patent Application No. 1750759-1, filed Jun. 15, 2017, the entire contents of each of which are incorporated herein by reference and relied upon.

TECHNICAL FIELD

The present disclosure relates to the technical field of providing microbiologically controlled fluids, and in particular to provide microbiologically controlled fluids that are suitable for dialysis.

BACKGROUND

It has become increasingly common to provide medical care for patients at the patients' homes. For patients suffering from renal failure, home therapies with peritoneal dialysis (PD) or haemodialysis (HD) are options that enable the patients to treat themselves at home and reduce the amount of medical centre visits.

Such dialysis treatments require dialysis fluids that typically have been provided ready to use in sealed, sterilized containers and delivered to the patient's home in 2-5 litres bags. A PD treatment requires between 8 and 20 litres of dialysis fluid per day, 7 days a week, 365 days a year for each patient. Considering the distribution effort to provide each patient with the containers and that many patients have difficulties to handle and store the containers, mixing or compounding of dialysis fluid at the point of care, e.g. at the patient's home, has been suggested. Concentrates are then mixed with water to become dialysis fluid at the point of care. The concentrates have to be provided to the point of care, but in a much smaller amount than the ready to use dialysis fluids. The concentrates are generally highly concentrated, 10-40× compared to ready to use fluids.

Automated PD normally uses a cycler for pumping the dialysis fluid to a patient and to remove used dialysis fluid from the patient. This is done via a cassette connected to lines leading to the dialysis fluid bags, the patient and the drain.

One of the major side-effects of PD is the risk for peritonitis which can have severe consequences for the patient and in the end result in that the patient cannot use PD treatment anymore. The risk for peritonitis is strongly connected to touch contamination during connection to peritoneum and the presence of microorganisms in the inflowing dialysis fluid. Patients are trained to perform the connections aseptically and with special care to avoid contamination.

Thus, in order to perform PD treatment successfully it is of vital importance to avoid all risks of contamination and risk of introducing microorganisms in the system, potentially reaching peritoneum, during treatment and preparation for treatment.

In the preparation of the dialysis fluid, and in line with above, water of a high purity level should be used. From U.S. Pat. No. 5,591,344A it is known to purify water, mix the purified water with concentrates to prepare a dialysis solution and use the dialysis solution in haemodialysis treatment. The membrane of the dialyzer serves as an additional barrier for any contaminants. According to U.S. Pat. No. 5,591,344A, bacteria will over time proliferate on the inner surfaces of the fluid circuits. To reduce such contamination, heat disinfection of the fluid circuit, including the extracorporeal lines, is performed. Water is heated to a high temperature and is circulated in the fluid circuit. As the fluid circuit includes the dialysis solution preparation with a chemical mixing tank, the water treatment and the extracorporeal dialysis modules, the amount of heated water and power needed to disinfect the fluid circuit is large and the heating process is time consuming.

US2015/0273090A1 discloses a water treatment device that provides water treated by means of a reverse osmosis filter. The treated water is transported to a haemodialysis apparatus for further mixing with additional substances. Heat disinfection is used to disinfect portions of the fluid path of the water treatment device.

SUMMARY

Some applications, e.g. PD, demand a very high purity of the dialysis solution. The purity of the dialysis solution has to be of such purity that it is suitable to be infused into the peritoneum.

It is an objective of the disclosure to provide a point of use system and method that enable microbiological control of the production of purified water to be used for providing dialysis fluid. It is a further objective to provide a cost efficient way of producing the purified water. It is a still further objective to provide a cost efficient way of producing the dialysis fluid. Another objective is to provide a point of use system and method that enable production of purified water that is suitable to be used in producing PD fluid. It is a further objective to provide a point of use system and method that enable production of the PD fluid.

These objectives and others are at least partly achieved by the independent claims, and by the embodiments according to the dependent claims.

According to a first aspect, the disclosure relates to a system comprising an integrated water purifying apparatus. The water purifying apparatus comprises a pre-filter circuit connected to a water inlet for receiving water from a water source, a particle filter and an activated carbon filter arranged to filter water received via the water inlet to produce pre-treated water. The water purifying apparatus further comprises a fluid circuit arranged to receive pre-treated water from the pre-filter circuit, the fluid circuit includes an RO-pump and a Reverse Osmosis, RO, device. The water purifying apparatus is further arranged to pump pre-treated water through the RO device using the RO-pump, to produce purified water, and output the purified water through the purified water outlet connector. The fluid circuit further includes a heating device arranged to heat purified water from the RO device to a temperature above 65° C. The water purifying apparatus is further arranged to heat disinfect the fluid circuit using the heated purified water. The system further comprises a line set connected to the purified water outlet connector at a water line connector of the line set. The line set includes at least one sterile sterilizing grade filter arranged to filter the purified water into sterile purified water.

The system provides microbiological control of the production of fluids for a dialysis treatment, especially dialysis fluid for PD. "Microbiological" and "microbial" are in this disclosure regarded as synonyms. As the water purifying apparatus can heat sterilize its fluid circuit, bacterial growth in the fluid circuit can be prevented. The at least one sterile sterilizing grade filter makes sure that the water from the water purifying apparatus is sterile. Thus, the system ensure continuous production of purified water with a high purity level, thus with no bacteria and a very low amount, i.e. concentration, of endotoxins.

According to some embodiments, the line set is a reusable line set. Thus, the line set can be used more than once. Between treatments, the line set should be rinsed and disinfected.

According to some embodiments, the fluid circuit is arranged to produce purified water with an amount of bacteria that is less than 100 Colony-Forming Units/mL and an amount of bacterial endotoxins that is less than 0.25 Endotoxin Units/mL. Thus, the water purifying apparatus is capable of producing purified water with a (microbial) purity level as of water for dialysis.

According to some embodiments, the at least one sterile sterilizing grade filter is arranged to filter the purified water into sterile purified water with an amount of bacteria that is zero Colony-Forming Units/mL and an amount of bacterial endotoxins that is less than 0.05 Endotoxin Units/mL. Thus, the at least one sterile sterilizing grade filter ensures sterility of the produced purified water.

According to some embodiments, the fluid circuit includes an Electro Deionization unit, EDI unit, arranged to further treat the purified water from the RO device and output further purified water, wherein the fluid circuit is arranged to output the purified water from the EDI unit through the water outlet connector. The EDI unit is capable of purifying the water from the RO device to have a conductivity level of less than 1.3 µs/cm at 25° C., and less than 1.1 µs/cm at 20° C.

According to some embodiments, the line set comprises a drain line connected at a drain line connector of the drain line to a drain connector of the water purifying apparatus, the water purifying apparatus further comprises a first drain path connected to the drain connector for transporting drain fluid received from the drain line of the line set to a drain. Thus, used fluid can be transported to a drain via the line set.

According to some embodiments, the water purifying apparatus further is arranged to heat disinfect the drain connector and the water outlet connector of the water purifying apparatus using the heated purified water. Thus, these connectors that may be exposed to contamination from outside of the water purifying apparatus can be heat disinfected whereby the microbiological control of the system is improved.

According to some embodiments, the water purifying apparatus comprises a control unit programmed to periodically instruct the water purifying apparatus to heat the purified water flowing in the fluid circuit by means of the heating device to a temperature above 65° C. and to control heat disinfection of the fluid circuit using the heated water such that a certain disinfection criterion is met. For example, the disinfection criterion may include meeting a certain time and temperature of the heat disinfection determined for example according to an A0 concept, as known in the art.

According to some embodiments, the control unit is programmed to instruct the water purifying apparatus to heat water flowing in the fluid circuit by means of the heating device and to output the heated water through the purified water outlet connector to the line set for heat disinfection of the line set. The water may also here be heated to a temperature above 65° C., such as between 85° C. and 95° C.

According to some embodiments, the system comprises at least one concentrate source, a cycler including a cycler control unit, a pump actuator arranged to be controlled by the control unit, wherein the line set is operable with the cycler and further comprises a pumping cassette having a pump chamber configured to be actuated by the pump actuator and a mixing container in fluid communication with the pumping cassette. Further, the cycler control unit comprises instructions for mixing the purified water and the at least one concentrate, the instructions include to cause the pump actuator to operate the pump chamber to pump a first amount of the purified water to the mixing container and cause the pump actuator to operate the pump chamber to pump a prescribed amount of the at least one concentrate from the at least one concentrate source to the mixing container. Optionally, the instructions include to also cause the pump actuator to operate the pump chamber to pump a second amount of the purified water to the mixing container. Thus, the system may be capable of preparing a dialysis fluid such as a PD fluid from the purified water and the concentrate(s). The prepared dialysis fluid will thus be suitable for PD if the concentrates are sterile and the purified water is sterile and non-pyrogenic.

According to some embodiments, the cycler control unit comprises instructions for performing a heat disinfection of the line set. The instructions include to cause the pump actuator to circulate hot water in the line set. The hot water is received from the water purifying apparatus. Thus, the line set may be heat disinfected such that it can be reused. In an example embodiment, the instructions include to cause the pump actuator to pull (i) hot water from the mixing container into the pump chamber, cause (ii) the pump actuator to operate the pump chamber to push the hot water into the mixing container, and repeat (i) and (ii) at least one time.

According to a second aspect, the disclosure relates to a method for producing microbiologically controlled fluid with a system. The system comprises a water purifying apparatus with a heat disinfected fluid circuit arranged for producing purified water, and a line set connected to a water outlet connector of the water purifying apparatus for transporting the purified water to a point of use. The method comprises treating water from a water source with a Reverse Osmosis unit, RO unit, of the fluid circuit to produce purified water with an amount of bacteria that is less than 100 Colony-Forming Units/mL and an amount of bacterial endotoxins that is less than 0.25 Endotoxin Units/mL. The method further comprises directing the purified water through the purified water outlet connector and the thereto connected line set including at least one sterile sterilizing grade filter, to produce sterile purified water with an amount of bacteria that is zero Colony-Forming Units/mL and an amount of bacterial endotoxins that is less than 0.05 Endotoxin Units/mL. Thus, purified water with a high level of purity can be continually produced. The combination of <100 Colony-Forming Units/mL purified water produced by the water purification apparatus along with the sterile sterilizing grade filter allow for the determination of a probably of a non-sterile unit (PNSU) for the purified water of less than $10^{-6}$ on a per treatment basis.

According to some embodiments, the system comprises a cycler, and the method further comprises causing a pump actuator of the cycler to operate a pump chamber of the line set to pump a first amount of the purified water to a mixing container of the line set, and causing the pump actuator to operate the pump chamber to pump a prescribed amount of at least one concentrate from at least one concentrate source to the mixing container. The at least one concentrate are sterile concentrates. Thus, sterile dialysis fluid can be produced using sterile concentrate and sterile purified water. Optionally, the method further comprises causing the pump actuator to operate the pump chamber to pump a second amount of the purified water to the mixing container.

According to some embodiments, the method further comprises heating the produced purified water to a temperature above 65° C., directing the heated purified water through the water outlet connector and circulating the heated purified water in the line set. Thus, the line set may be heat disinfected such that it can be reused.

According to some embodiments, the method comprises treating the purified water from the RO-unit with an electrodeionization, EDI, unit. The produced purified water from the EDI makes it possible to produce water for injection.

According to a fourth aspect, the disclosure relates to a computer program comprising instructions which, when the program is executed by a control unit, cause the control unit and an thereto associated water producing apparatus to carry out the method as described herein.

According to a fifth aspect, the disclosure relates to a computer-readable medium comprising instructions which, when executed by a control unit, cause the control unit and a thereto associated water producing apparatus to carry out the method.

DETAILED DESCRIPTION

In the following a system for producing microbiologically controlled fluids will be explained. The system is intended to be used in applications requiring fluids with a high purity level. Such an application is peritoneal dialysis (PD). The risk of microbiological contamination makes it a challenge to produce PD fluids at patients' home. The system should to be designed in such a way that it reduces risk of biofilm formation in the fluid path, reduces microbiological contamination during connection and secures the microbiological control. A ready to use solution should be free from microorganisms and essentially free from bacterial endotoxins.

The disclosure provides in a first aspect a system that provides purified water with a high degree of purity. This is achieved with a heat disinfected water purification apparatus and a line set comprising at least one sterile sterilizing grade filter. The line set is in one embodiment pre-sterilized. The at least one filter is then at least one sterile sterilizing grade filter. In an extended first aspect, the system includes a cycler for providing dialysis fluid with a high degree of purity by mixing the purified water with at least one concentrate. The at least one concentrate is in one embodiment pre-sterilized. The provided dialysis fluid is free from bacteria and essentially free from bacterial endotoxins, thus non-pyrogenic.

The disclosure provides a system and methods to maintain the microbiological control of the system, such that the system can be used continually with maintained purity degree of the produced fluid(s).

The water purification apparatus may in-between treatments be heat disinfected using hot water. This procedure disinfects the fluid circuit including the RO membrane and the fluid path downstream the RO membrane. Frequent hot water disinfection makes it possible to design away from build-up of biofilm in the fluid path, reduces the risk of endotoxin contamination and overall minimizes bioburden of the system.

Figure 1:
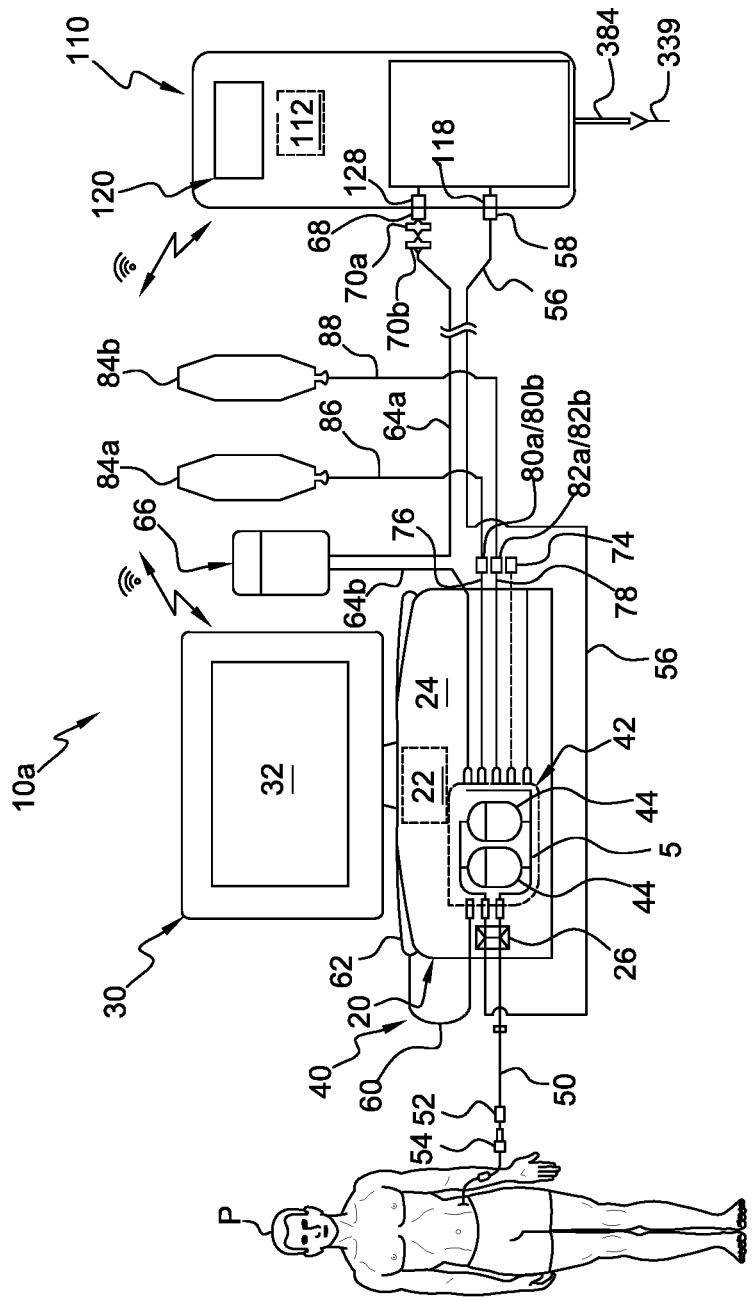
FIG. 1 illustrates an exemplary PD system.

An exemplary system 10a will now be described with reference to FIGS. 1 and 4. FIG. 1 illustrates the exemplary system 10a being a peritoneal dialysis system having point of use dialysis fluid production. The system 10a includes a cycler 20 and a water purifiying apparatus 110. Suitable cyclers for cycler 20 include, e.g., the Amia® or HomeChoice® cycler marketed by Baxter International Inc., with the understanding that those cyclers need updated programming to perform and use the point of use dialysis fluid produced according to system 10a. To this end, cycler 20 includes a control unit 22 including at least one processor and at least one memory. Control unit 22 further includes a wired or wireless transceiver for sending information to and receiving information from the water purifying apparatus 110. The water purifying apparatus 110 also includes a control unit 112 including at least one processor and at least one memory. Control unit 112 further includes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier apparatus 112 includes a first drain path 384 connected to the drain connector 118 for transporting drain fluid received from the drain line 56 to a drain 339. The drain 339 may be a housing drain or drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump actuator 5 each under control of control unit 22, or a single pump actuator 5 creating both positive and negative pressure under control of control unit 22, for providing positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off solenoid pneumatic valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (viii) an occluder 26 under control of control unit 22 for closing the patient and drain lines in alarm and other situations.

In an exemplary embodiment, the plural pneumatic valve chambers and the plural pneumatic pump chambers are located on a front face or surface of housing 24 of cycler 20. The heater is located inside housing 24 and in an embodiment includes heating coils that contact a heating pan, which is located at the top of housing 24, beneath a heating lid (not seen in FIG. 1).

Cycler 20 in the illustrated embodiment includes a user interface 30. User interface 30 may also include one or more electromechanical input device, such as a membrane switch or other button, or a video monitor 32 optionally overlaid with a touch screen. Water purifier 110 in the illustrated embodiment also includes a user interface 120. User interface 120 may also include one or more electromechanical input device, such as a membrane switch or other button, or a video monitor optionally overlaid with a touch screen.

Figure 4:
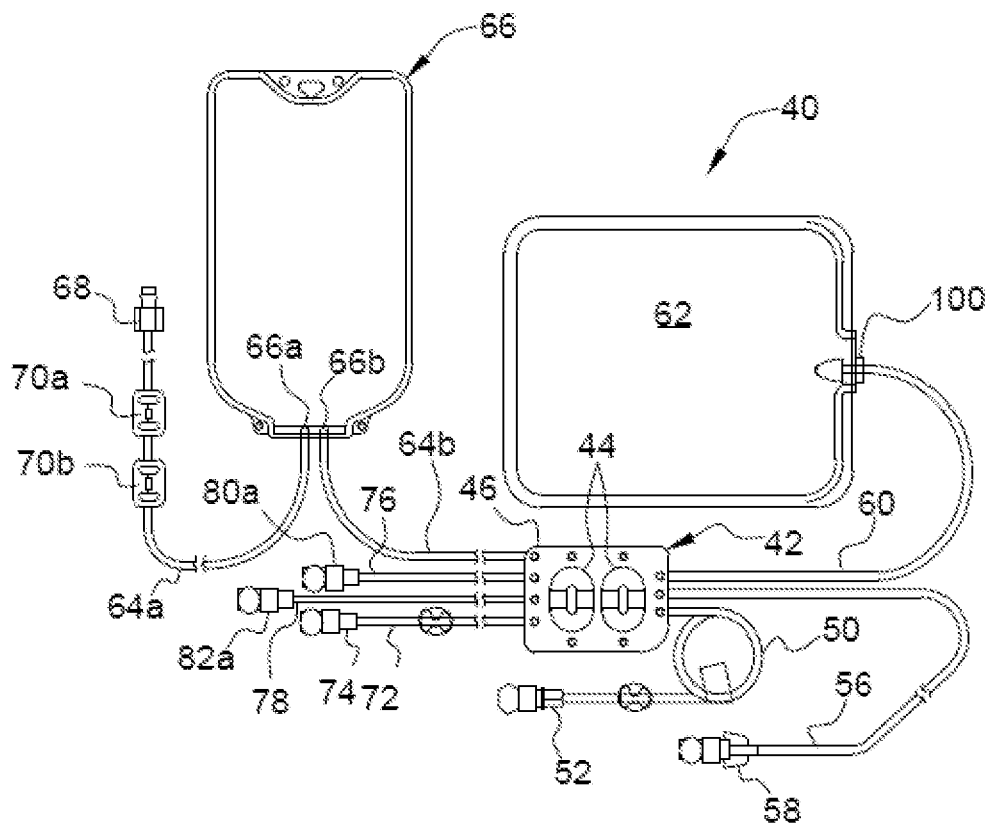
FIG. 4 illustrates the line set in isolation according to some embodiments.

Referring additionally to FIG. 4, one exemplary embodiment of disposable line set 40 is illustrated. Disposable set 40 is also illustrated in FIG. 1, mated to cycler 20 to move fluid within the disposable line set 40, e.g., to mix dialysis fluid as discussed herein. Disposable line set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. FIG. 4 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20. In an example embodiment, the line set 40 is a reusable line set. Thus, the line set 40 may be reused one or more times before it is exchanged for another line set 40. The line set 40 my thus be seen as semi-disposable, as it can be used more than once. The line set 40 is delivered to the user in a sterile format.

FIGS. 1 and 4 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. FIG. 1 illustrates that drain line connector 58 is connected removeably to a drain connector 118 of the water purifying apparatus 110.

FIGS. 1 and 4 further illustrate that disposable set 40 includes a heater/mixing line 60 that extends from a heater/mixing line port of cassette 42 and terminates at a heater/mixing container 62 (or bag). Disposable set 40 includes an upstream water line segment 64a that extends to a water inlet 66a of water accumulator 66. A downstream water line segment 64b extends from a water outlet 66b of water accumulator 66 to cassette 42. In the illustrated embodiment, upstream water line segment 64a begins at a water line connector 68 and is located upstream from water accumulator 66. FIG. 1 illustrates that water line connector 68 is removeably connected to a water outlet connector 128 of water purifier 110.

Water purifier 110 outputs water and possibly water suitable for peritoneal dialysis ("WFPD"). WFPD is purified water suitable for making dialysis fluid for delivery to the peritoneal cavity of patient P. To ensure WFPD, however, a sterile sterilizing grade filter 70a is placed upstream from a downstream sterile sterilizing grade filter 70b, respectively. Filters 70a and 70b may be placed in water line segment 64a upstream of water accumulator 66. Sterile sterilizing grade filters 70a and 70b may be pass-through filters that do not have a reject line.

In an example embodiment, the at least one sterile sterilizing grade filter 70a, 70b is arranged to filter the purified water into sterile purified water with an amount of bacteria that is zero Colony-Forming Units/mL (CFU/mL) and an amount of bacterial endotoxins that is less than 0.05 Endotoxin Units/mL (EU/mL). The sterilizing grade filters ensures that the water used to prepare the PD fluid for administration meets requirements for sterile non-pyrogenic water. The sterile sterilizing grade filters includes a membrane having pores with average diameters suitable to produce sterile fluid, including the capability of removing endotoxins, resulting in water quality suitable for PD. The sterile sterilizing grade filters provide the final stage of sterilization for the water that is used to mix with the one or more concentrate to provide a dialysis fluid suitable for PD. The mean pore diameter for sterile sterilizing grade filter may, for example, be less than one micrometre, such as 0.1-0.5 micrometre, e.g. 0.1 or 0.2 micrometre. Bacteria typically have a diameter of a few micrometres, and will then not pass through the pores. The filter membrane may further comprise a high molecular weight additive bearing cationic charges, for example a cationic charged polymer. Examples of other kinds of positively charged additives can be found in EP1710011A1. The filter membrane will thus be positively charged. The membrane will then reject bacterial endotoxins, whereby less bacterial endotoxins will pass the membrane. In an exemplary embodiment, bacteria and bacterial endotoxins will also be retained based on adsorption to the membrane. The membrane may be polyethersulfone-based. Other suitable polymers may be AN69, PAN, PMMA, cellulose etc. Suitable sterile sterilizing grade filters 70a and 70b may, for example, be Pall IV-5 or GVS Speedflow filters, or be filters provided by the assignee of the present disclosure. In an exemplary embodiment, only one upstream or downstream sterile sterilizing grade filter 70a and 70b is needed to produce WFPD, nevertheless, two sterile sterilizing grade filters 70a and 70b are provided for redundancy in case one fails.

The purified water will then be sterile and have a very low amount of bacterial endotoxins before it is mixed with concentrates when preparing ready to use fluid.

FIG. 4 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 4 illustrate that disposable set 40 includes a first, e.g., glucose, concentrate line 76 extending from a first concentrate port of cassette 42 and terminates at a first, e.g., glucose, cassette concentrate connector 80a. A second, e.g., buffer, concentrate line 78 extends from a second concentrate port of cassette 42 and terminates at a second, e.g., buffer, cassette concentrate connector 82a.

FIG. 1 illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

In an embodiment, to begin treatment, patient P loads cassette 42 into cycler and in a random or designated order (i) places heater/mixing container 62 onto cycler 20, (ii) connects upstream water line segment 64a to water outlet connector 128 of water purifier 110, (iii) connects drain line 56 to drain connector 118 of water purifier 110, (iv) connects first cassette concentrate connector 80a to first container concentrate connector 80b, and (v) connects second cassette concentrate connector 82a to second container concentrate connector 82b. At this point, patient connector 52 is still capped. Once fresh dialysis fluid is prepared as described in detail below, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

For disposable set 40, the rigid portion of cassette 42 may be made for example of a thermal olefin polymer of amorphous structure ("TOPAS") cyclic olefin copolymer ("coc"). The flexible membranes of cassette 42 may be made for example of a copolyletser ether ("PCCE") and may be of one or more layer. Any of the tubing or lines may be made for example of polyvinyl chloride ("PVC"). Any of the connectors may be made for example of acrylonitrile-butadiene-styrene ("ABS", e.g., for concentrate connectors 80a, 80b, 82a, 82b and heater/mixing bag connector 100 discussed below), acrylic (e.g., for drain line connector 58) or PVC (e.g., for water line connector water line connector 68). Any of the bags or containers may be made of PVC. The materials for any of the above components may be changed over time.

FIG. 1 illustrates that water line connector 68 is removeably connected to a water outlet connector 128 of water purifier 110. The drain line 56 is removeably connected to a drain connector 118 of water purifier 110.

The control unit 22 of the cycler comprises instructions for mixing the purified water and the at least one concentrate into a PD fluid. The instructions includes to i) cause the pump actuator 5 to operate the pump chamber 44 to pump a first amount of the purified water to the mixing container 62 and ii) cause the pump actuator 5 to operate the pump chamber 44 to pump a prescribed amount of the at least one concentrate from the at least one concentrate source 84a, 84b to the mixing container 62. In one embodiment, the instructions further comprises to iii) cause the pump actuator 5 to operate the pump chamber 44 to pump a second amount of the purified water to the mixing container 62. According to an example embodiment, the first and second amounts of the purified water add to a total amount needed for the PD fluid.

Figure 2:
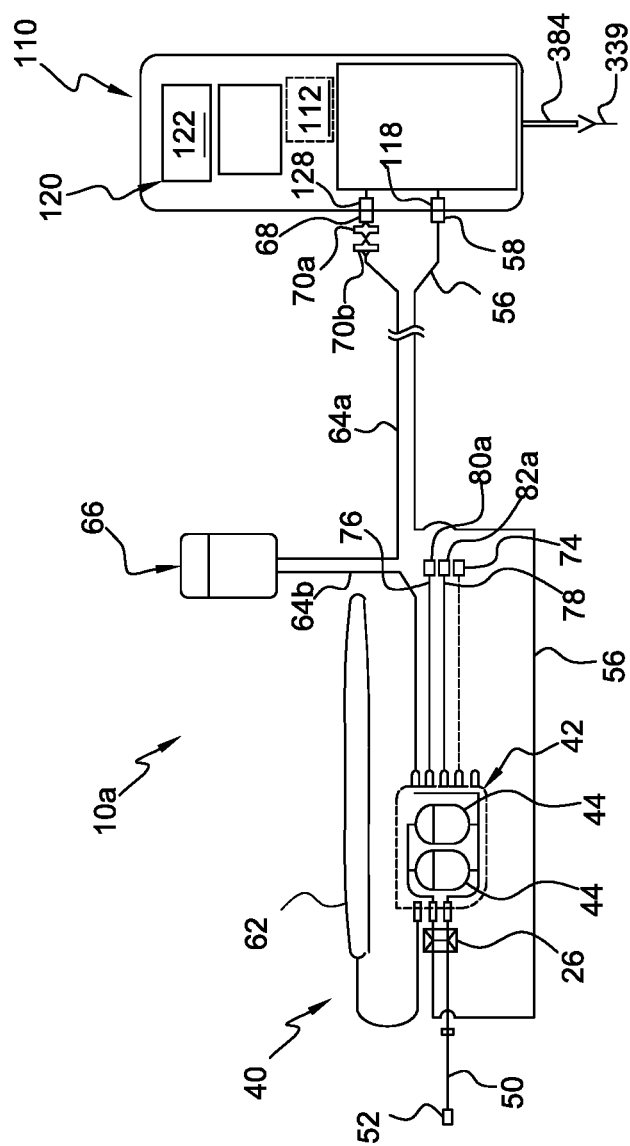
FIG. 2 illustrates a system comprising a water purifying apparatus and a line set according to some embodiments.

FIG. 2 illustrates the system 10a according to one example embodiment where the system 10a comprises the water purification apparatus 110 and the line set 40 connected to the drain connector 118 and the water outlet connector 128 in isolation.

Figure 3:
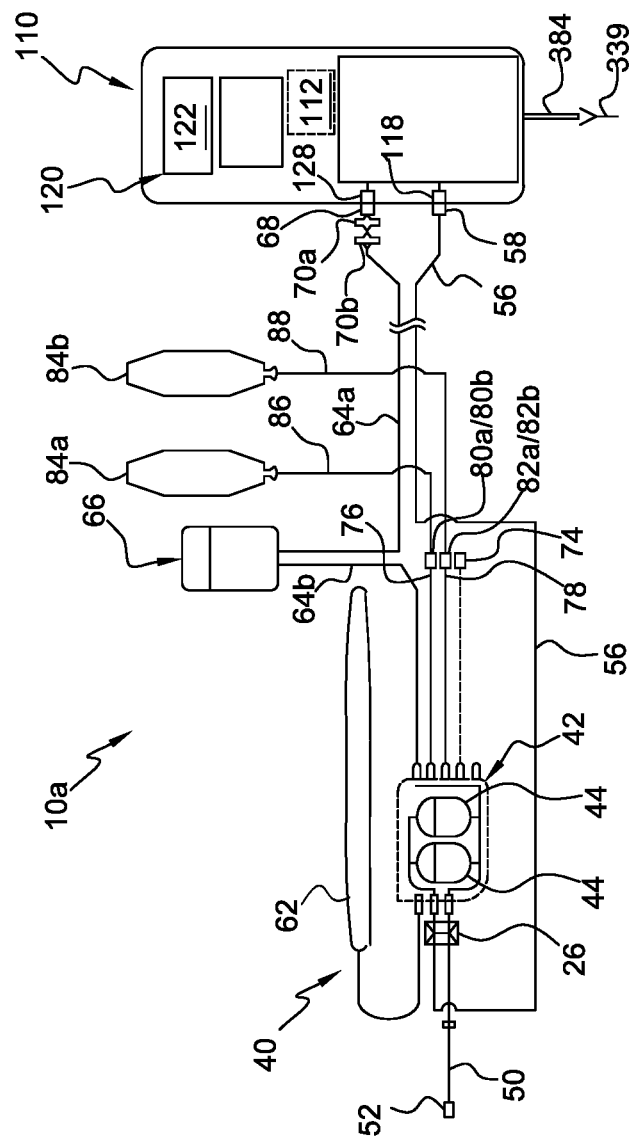
FIG. 3 illustrates the system in FIG. 2 with connected concentrate containers.

FIG. 3 illustrates the system 10a according to one example embodiment where the system 10a illustrated in FIG. 2, where the system 10a further comprises the first concentrate container 84a and the second concentrate container 84b connected to the line set 40.

The line set 40 including the cassette 42, and also the concentrates in the containers 84a, 84b, are sterilized during manufacture and delivered to the patient's home as sterile disposables that may be discarded after being used once. In one embodiment, the line set 40 may be used more than once and thus re-used two or three times. The line set 40 may then be referred to as semi-disposable. In some embodiments, also the containers 84a, 84b with concentrates are used more than once, such as two or three times.

FIG. 4 is a schematic of the functional parts of the water purification apparatus 110 according to one exemplary embodiment, including a pre-treatment module 160, a reverse-osmosis (RO) module 170 and a post-treatment module 180. The water purification apparatus 110 comprises an inlet port 399 for feeding water from a water source 398, e.g. a water tap, into the water purification apparatus 110, for purification of the water. The incoming water from the water source is fed through the inlet port 399 into the pre-treatment module 160.

The Pre-Treatment Module

The Pre-treatment module 160 treats the incoming water with a particle filter and a bed of activated carbon. The particle filter is arranged to remove particles such as clay, silt and silicon from the incoming water. The particle filter is arranged to prohibit particles in the size of micro meter, optionally also larger endotoxin molecules, from the incoming water. The bed of activated carbon is arranged to remove chlorine and compositions with chlorine from the incoming water, and to absorb toxic substances and pesticides. In an example embodiment, the bed of activated carbon is arranged to remove one or several of hypochlorite, chloramine and chlorine. In a further example embodiment, the bed of activated carbon is also arranged to reduce organic compounds (TOC total organic carbon) including pesticides of the incoming water.

In an exemplary embodiment, the particle filter and the bed of activated carbon are integrated in one single consumable part. The consumable part is for example exchanged on a predefined interval dependent on the incoming water quality. The quality of the incoming water is for example examined and determined by qualified people before the first use of the water purification apparatus 110 at a point of care.

Optionally the pre-treatment module 160 comprises an ion exchange device for protection of downstream located devices such as a Reverse Osmosis, RO, membrane and a polisher.

The pre-treatment module 160 thus filters the incoming water and delivers pre-treated water to a downstream located RO-module 170.

RO-Module

The RO-module 170 removes impurities from the pre-treated water, such as microorganisms, pyrogens and ionic material from the pre-treated water by the effect of reverse osmosis. The pre-treated water is pressurized by a pump and forced through RO-membrane to overcome the osmotic pressure. The RO-membrane is for example a semi-permeable membrane. Thereby the stream of pre-treated water, called feed water, is divided into a reject stream of water and a stream of permeate water. In an example embodiment, the reject water may be passed via a one or both of a first reject path and a second reject path. The first reject path recirculates reject water back to the feed fluid path of the RO-pump in order to be fed back into RO-device again. The recirculated reject water increases the feed flow to the RO-device, to get a sufficient flow past the reject side of the RO-membrane to minimize scaling and fouling of the RO-membrane. The second reject path directs reject water to drain. This makes the concentration level on the reject side to be sufficiently low to get an appropriate, required, permeate fluid concentration. If the feed water has low content of solutes, part of the drain flow can also be directed back to the inlet side of the RO-membrane and thereby increasing the water efficiency of the water purification apparatus 110. The RO-module 170 thus treats the pre-treated water and delivers permeate water to a downstream located post-treatment module 180. In particular, the RO-device reduces the conductivity of the pre-treated water with 96-99%. For example, if the pre-treated water received to the RO-device has a conductivity of 200-500 µS/cm, the RO-device reduces this amount to about 10-20 µS/cm. The permeate water, thus the purified water from the RO-device, will have a conductivity of about 10-20 µS/cm. According to one exemplary embodiment, the RO-device is capable of purifying the permeate water to have a conductivity of maximum 30 µS/cm. In particular, the RO-device is capable of purifying the permeate water to have a conductivity of maximum 15 µS/cm.

Post-Treatment Module

The post-treatment module 180 polishes the permeate water in order to further remove ions from the permeate water. The permeate water is polished using a polisher device such as an Electrodeionization, EDI, device or a mixed bed filter device. The EDI-device makes use of electrodeionization for removing ions, from the permeate water, such as aluminum, lead, cadmium, chromium, sodium and/or potassium etc., which have penetrated the RO-membrane. The EDI-device utilizes electricity, ion exchange membranes and resin to deionize the permeate water and separate dissolved ions, i.e. impurities, from the permeate water. The EDI-device produce polished water, polished by the EDI-device to a higher purity level than the purity level of the permeate water. The EDI may have an anti-bacterial effect of the product water and can reduce the amount of bacteria and bacterial endotoxins in the water due to, among other, the electrical field in the EDI-device. The mixed bed filter device comprises a column, or container, with a mixed bed ion exchange material.

The polished water, herein also referred to as product water, is thereafter ready for being delivered from a water outlet connector 128 of the water purification apparatus 110 to a point of use of the product water. The product water is suitable for dialysis, i.e. water for dialysis. In one embodiment, the product water is suitable for injection, i.e. water for injection. The drain connector 118 is in one example embodiment used for receiving used fluid, e.g. from a PD patient, via a drain line 64, for further transport via a first drain path 384 of the water purification apparatus 110 to a drain 339 of the water purification apparatus 110. In particular, the polisher device reduces the conductivity of the permeate water to 96-99%. For example, if the permeate water received to the polisher device has a conductivity of 10-20 µS/cm, the polisher device reduces this amount to about 0.30 µS/cm. The polished water, thus the purified water from the polisher device, will thus have a conductivity of about 0.30 µS/cm. According to one exemplary embodiment, the polisher device is capable of purifying the water to have a conductivity less than 1.3 µS/cm at 25° C. In one example embodiment, the water purifying apparatus 110 does not include the polisher device such as the EDI unit 306, but is capable of producing water for dialysis.

The minimum requirements for water for haemodialysis and related therapies are defined in ANSI/AAMI 13959: 2014 and ISO 13959:2014. The requirements include limits on a plurality of contaminants, such as chlorine, bacteria, bacterial endotoxins, chemical contaminants and heavy metal. For example, the amount of chlorine/chloramine should be less than 0.1 mg/L, the amount of bacteria shall be less than 100 CFU/mL and the amount of bacterial endotoxins shall be less than 0.25 EU/mL.

The requirements for water for injection is for example defined in the Official Monographs for water, United States Pharmacopeia (USP) 39 National Formulary (NF) 34 (Aug. 1, 2016). The requirements include recommended temperature dependent limits on the water conductivity, the amount of Total Organic Carbon and amount of bacterial endotoxins. The limit on water conductivity is defined in USP 645 (Aug. 1, 2016). For example, at 20° C. the conductivity of the water should be less than 1.1 µS/cm, at 25° C. the conductivity of the water should be less than 1.3 µS/cm etc. The amount of Total Organic Carbon (TOC) should be less than 0.5 mg/L (500 ppb), the amount of bacteria should be less than 10 CFU/mL and the amount of bacterial endotoxins should be less than 0.25 EU/mL.

In order to produce WFPD, the limits on bacteria and bacterial endotoxins are even more demanding. The amount of bacteria should be zero CFU/mL, thus, the water has to be sterile. The amount of bacterial endotoxins should be less than 0.05 EU/mL. In other words, the sterile purified water should be non-pyrogenic.

In one exemplary embodiment, the water outlet connector 128 and the drain connector 118 are recessed in the cabinet wall of the water purification apparatus 110. Also, a door (not shown) covers the connectors 118, 128 when the connectors 118, 128 are not connected to the line set 40. Thereby the connectors 118, 128 are more shielded from contamination from the exterior, such as touch contamination and dust.

The disposable line set 40 is arranged with at least one sterile sterilizing grade filter set 70a, 70b, for filtering the product water from the water purification apparatus 110 to ensure sterility of the produced purified water, and a very low amount of bacterial endotoxins. Thus, the product water collected in the accumulator bag 66 has passed through one or several sterile sterilizing grade filters of the disposable line set 40 for removal of bacteria and bacterial endotoxins, i.e. to produce sterile purified water. According to one embodiment, the sterile sterilizing grade filters are redundant. By collecting the sterile product water in the accumulator bag 66, the water purification apparatus 110 and the cycler 20 are decoupled in terms of pressure, so that the high pressure needed to push water through the sterile sterilizing grade filters does not affect the cycler 20. The at least one sterile sterilizing grade filter 70a, 70b ensures that the water used to prepare the PD fluid for administration meets requirements for sterile, non-pyrogenic water (0 CFU/mL and <0.05 EU/mL).

Figure 5:
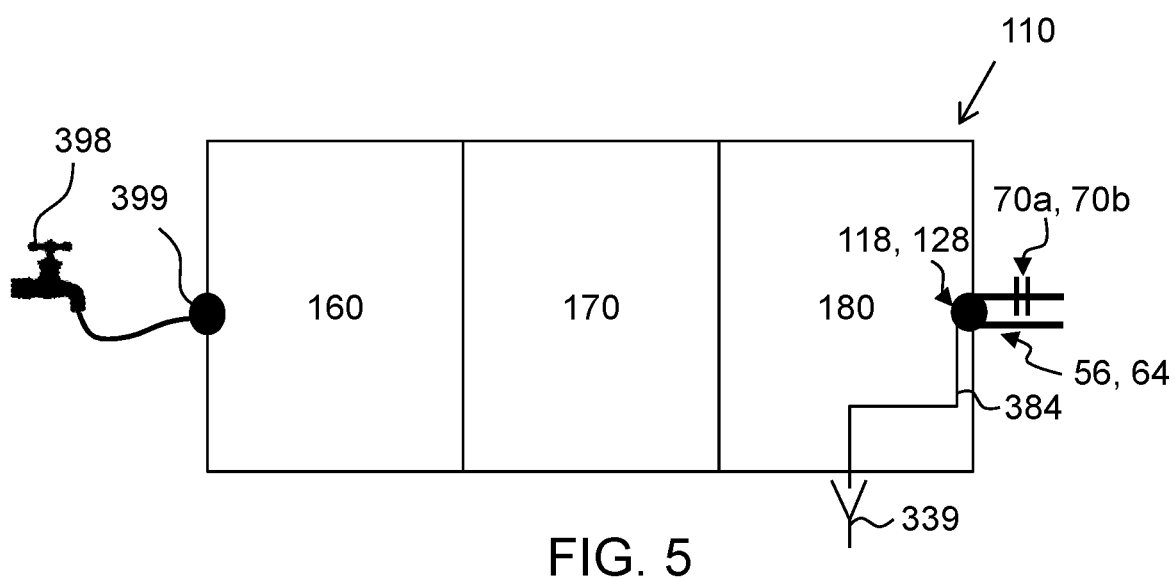
FIG. 5 illustrates a modular view of the water purifying apparatus according to some embodiments.
Figure 6:
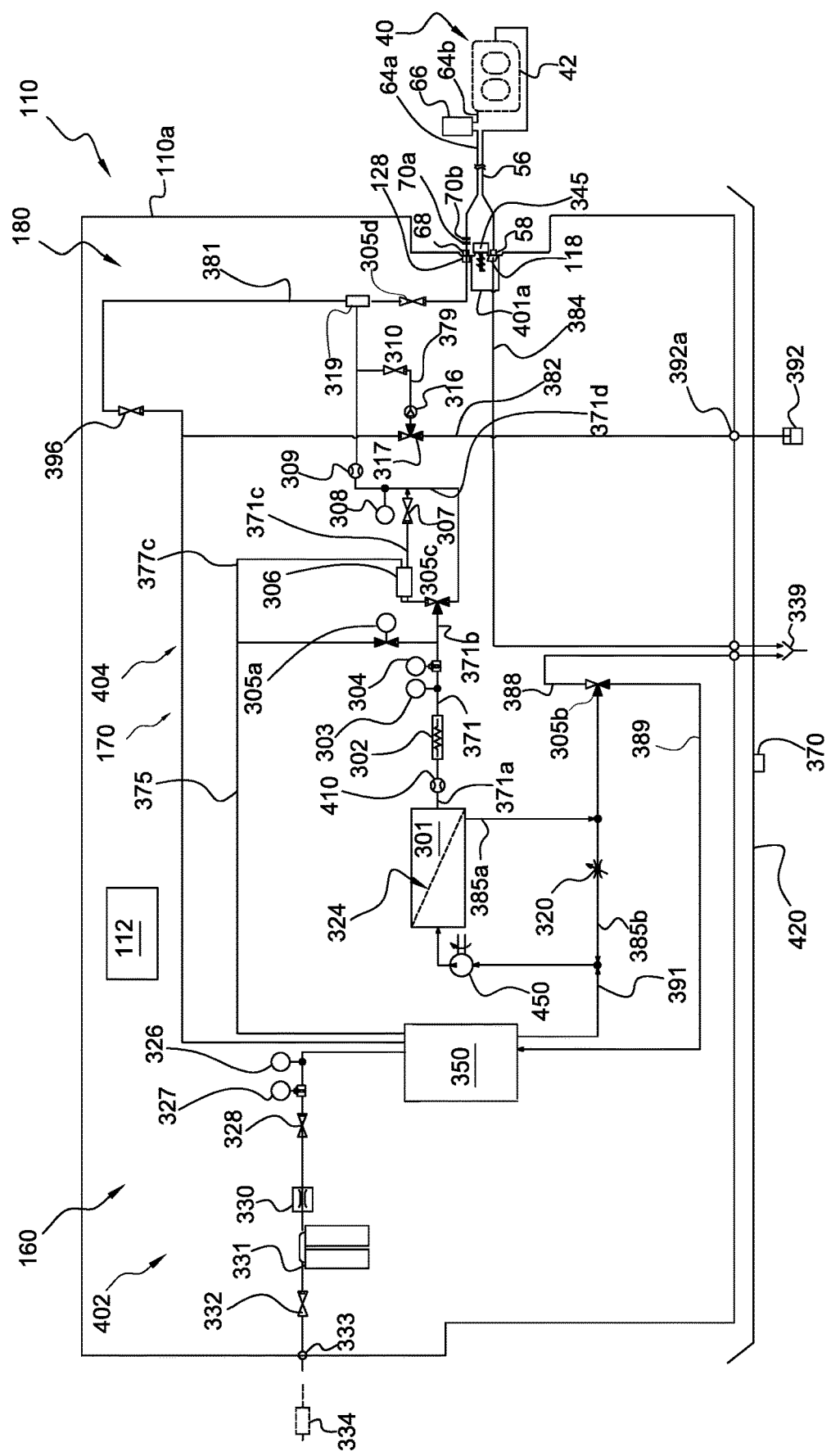
FIG. 6 illustrates the water purifying apparatus according to some embodiments.

FIG. 6 illustrates an example embodiment of the water purification apparatus 110. In other embodiments, the water purification apparatus 110 may include less or more components or modules. The water purification apparatus 110 of FIG. 6 receives water from a water source 398 (FIG. 5), such as a continuous source of potable or drinkable water from a patient's home. In various embodiments, water purification apparatus 110 may be installed in a room having access to the water source 398 to provide WFPD to cycler 20 as discussed herein. The water is optionally pre-filtered using a particle pre-filter 334 to remove dirt and sediment, before it is delivered to the water purification apparatus 110. The water enters the water purification apparatus 110 via the water inlet port 333. As previously described, the water purification apparatus 110 includes a pre-treatment module 160, a RO module 170 and a post-treatment module 180. The pre-treatment module 160 includes a pre-filter circuit 402 connected to a water inlet 333 for receiving water from the water source 398, a particle filter and an activated carbon filter, i.e. a bed of activated carbon, arranged to filter water received via the water inlet 333 to produce pre-treated water. The particle filter and the activated carbon filter are embodied in one single filter package 331. The single package 331 is a disposable package. The pre-filter circuit 402 may also comprise a softener using for example ion exchange. The pre-filter circuit 402 includes an inlet valve 332 and a constant flow device 330 upstream the filter package 331. The inlet valve 332 controls the feed water inflow by control of the control unit 112. The constant flow device 330 provides a constant flow to the tank 350 providing that the water pressure is above a minimum pressure for constant flow device 330. Further, the pre-filter circuit 402 comprises a tank valve 328, a pre-treatment conductivity sensor 327 and a feed water temperature sensor 326 downstream the filter package 331. The tank valve 328 controls the flow of pre-treated water to the tank 350. The pre-treatment conductivity sensor 327 monitors the conductivity of the pre-treated water, and the water temperature sensor 326 monitors the temperature of the pre-treated water. The temperature of the pre-treated water is for example needed to calibrate the conductivity measurement of the pre-treated water. The pre-treatment circuit 402 is connected to the water inlet port 333 and ends into the tank 350. The inlet valve 332 and the tank valve 328 are configured to be controlled by the control unit 112 of the water purification apparatus 110. Water softening in the pre-treatment circuit 402 may alternatively or additionally be achieved using lime softening, ion-exchange resins or an anti-scalant such as polyphosphate, as known in the art.

The water purifying apparatus 110 further comprises a fluid circuit 404 arranged to receive pre-treated water from the pre-filter circuit 402. The fluid circuit 404 comprises at least some of the parts of the RO module 170 and at least some of the parts of the post-treatment module 180. In particular, the fluid circuit 404 comprises an RO-pump 450 and a Reverse Osmosis, RO, device, 301. The fluid circuit 404 also comprises the tank 350. The water purifying apparatus 110 is further arranged to pump pre-treated water through the RO device 301 using the RO-pump 450, to produce purified water, and output the purified water through a water outlet connector 128. In an exemplary embodiment, the fluid circuit 404 is arranged to produce purified water with an amount of bacteria that is less than 100 CFU/mL and an amount of bacterial endotoxins that is less than 0.25 EU/mL. This is achieved by means of the RO device 301. The polisher device, such as the EDI device 306, may be capable of further reducing the amount of bacteria and bacterial endotoxins.

A RO-device 301 has already been described in detail with reference to the FIG. 5 and reference is made to that description for further explanation. The pre-treated water enters the tank 350, for example from an upper part of the tank 350. Pre-treated water is accumulated in the tank 350 and pumped by the RO-pump 450 to the feed inlet 301a of the RO-device 301. A line 391 is connected to the bottom of the tank 350 and the feed inlet 301a. The RO-pump 450 is fitted to the line 391.

The RO-pump 450 is configured, under control of the control unit 112, to provide the water flow and pressure requisite for the reverse osmosis process taking place at RO-device 301. As previously described e.g. with reference to FIG. 5, the RO-device 301 filters water to provide purified water at its permeate outlet 301b. Reject water leaving RO-device 301 at a reject outlet 301c (the reject water may be fed back into RO-pump 450 to conserve water consumption or alternatively be pumped to drain 339).

Purified water leaving the RO-device 301 is transported in a purified fluid circuit 371, of the fluid circuit 404, inside the water purification apparatus 110 before being output through the water outlet connector 128, that is, a port. The purified fluid circuit comprises permeate fluid path 371a, polisher fluid path 371b and product fluid path 371c. The EDI-device 306 may be by-passed via the bypass path 371d. The bypass path 371d is connected to the purified fluid circuit 371 upstream the EDI-device 306, and to the purified fluid circuit downstream the EDI-device 306. Purified water leaving the RO-device 301 passes a flow sensor 410, a heating device 302, and a permeate temperature sensor 303, included in the permeate fluid path 371a. The flow sensor 410 monitors the flow of the purified fluid leaving the RO-device 301. The heating device 302, heats, by control of the control unit 112, the purified water leaving the RO-device 301. The permeate temperature sensor 303 monitors the temperature of the purified fluid leaving the RO-device 301 directly downstream the heating device 302. An additional conductivity sensor 304 monitors the conductivity of purified water leaving RO-device 301.

Downstream the heating device 302, the permeate temperature sensor 303 and the additional conductivity sensor 304, the purified fluid enters the post-treatment module 180 via the polisher fluid path 371b. The post-treatment module 180 comprises the polisher device, e.g. the EDI-device 306. The three-way valve 305c is arranged to be controlled by the control unit 112 to selectively direct the purified fluid flow into either the EDI-device 306, or into the bypass path 371d in order to bypass the EDT-device 306. When directed to the EDI-device 306, the purified fluid enters the product channel 306a, the concentrate channel 306b and the electrode channel 306c of the EDI-device 306. The purified fluid is fed to all the channels via the polisher fluid path 371b downstream the three-way valve 305c. The EDI-device 306 is configured to produce purified water, here also referred to as product water. The produced product water leaves the EDI-device 306 and enters the product fluid path 371c. A product channel valve 307 regulates the flow rate of the product water in the product fluid path 371c from the product channel 306a. The concentrate fluid path 377c is arranged to pass concentrate water and the electrode fluid back to the tank 350. Thus, the fluid circuit 404 may include an EDI unit, 306 arranged to further treat the purified water from the RO device 301 and output further purified water. The fluid circuit 404 is arranged to output the purified water from the EDI unit 306 through the water outlet connector 128. The purified water is thus passed to the water outlet connector 128, and further into a thereto connected water line 64 (64a, 64b) of the fluid line set 40 for transport to the point of care. The fluid line set 40 comprises two sterile sterilization filters 70a, 70b. The sterile sterilization filters 70a, 70b filter the product water leaving the water outlet connector 128 into sterilized product water that is suitable for injection. According to some alternative embodiments the number of filters is less or more than two.

A drain connector 118 defines a first drain path 384 to the drain 339. A drain line 56 of the fluid line set 40 is connected to the drain connector 118, in order to pass fluid, such as used PD-fluid, from the drain connector 118 to the drain 339. The first drain path 384 here embodies the part of a cycler drain path that is present inside the water purification apparatus 110.

The flow control device 305*a* is configured to control the flow rate of purified water in the recirculation path 375 arranged from a point downstream the heater 302, the permeate temperature sensor 303 and the additional conductivity sensor 304, and back to the tank 350. A product water pressure sensor 308 is arranged to monitor the pressure in the product fluid path 371*c* downstream the EDI-device 306. A product water flow sensor 309 is arranged to monitor the flow rate of the product water downstream the EDI-device 306. The pressure and the flow rate of the product water are feed to the control unit 112. The control unit 112 is configured to control the operation of the flow control device 305*a*. More particularly the control unit is configured to regulate the flow rate in the recirculation path 375 based on the pressure and flow rate of the product water, in order to control the flow rate of the product water to a desired flow rate, and the pressure of the product water to a desired pressure. The flow control device 305*a* is for example a motorized flow control valve that is configured to finely regulate the flow rate in the recirculation path 375.

A product water valve 305*d* is arranged to, by control of the control unit 112, control the produced product flow to go to either the water outlet connector 128, or back to the tank 350 via an additional recirculation path, here a first recirculation path 381. An emptying valve 396 is arranged to control the flow rate in the first recirculation path 381. The first recirculation path 381 is fluidly connected to the product fluid path 371*c* via an air-trap chamber 319. A product water conductivity sensor 312 is arranged to monitor the conductivity of the product water upstream the air-trap chamber 319. A product fluid temperature sensor 313 is configured to monitor the temperature of the product water upstream the air-trap chamber 319.

In operation, a portion of the rejected water leaves the RO-device 301 via a fluid path 385*a* and a three-way valve 305*b* (e.g. a three-way solenoid valve) under control of control unit 112. A remaining portion of the rejected water returns to RO-pump 450 via a valve 320 (e.g., a manual needle valve) in a first reject path 385*b*. Three-way valve 305*b* is configured to selectively divert the rejected water either to drain 339 via a second drain path 388 or back to tank 350 via a second reject path 389.

All meters and sensors described in connection with water purification apparatus 110 in FIG. 6 are configured to send their corresponding signals to control unit 112.

The water purification apparatus 110 includes a container 392 containing a microbiological growth inhibiting agent. As illustrated, container 392 is in fluid communication with an inlet 392*a* of the water purification apparatus 110. In FIG. 6, the chemical intake path 382 connects container 392 to the fluid path of the water purification apparatus 110. Alternatively, container 392 may be connected via a line (not illustrated) leading directly to disposable cassette 42 operating with cycler 20, or be connected to water line 64, or be connected to drain line 56. The agent inhibiting microbiological growth in the container 392 may be a suitable physiologically safe acid, such as citric acid, citrate, lactic acid, acetic acid, or hydrochloric acid (or a combination thereof). In one embodiment, container 392 contains citric acid, citrate or a derivative thereof. It is noted that container 392 may also include additives provided together with the acid (such as with citric acid). The chemical inlet 392*a*, is located for example at the front of water purification apparatus 110. The three-way valve 317, under control of control unit 112, at chemical inlet 392*a* is arranged to open towards a second pump 316 being a chemical intake pump, and tank 350. The second pump 316 is arranged to feed disinfecting solution into tank 350. Three-way valve 317 under control of control unit 112 may also be used to recirculate water and disinfectant from and to tank 350 during the phases of chemical disinfection (i.e. disinfection with a cleaning agent), cleaning and/or rinse. The second pump 316 and a valve 310 are arranged in a path 379 fluidly connecting the three-way valve 317 and the product fluid path 371*c*. The valve 310 is arranged to control the flow in the path 379.

In a more detailed disinfection phase example, when chemical disinfection is initiated, the level in tank 350 is adjusted to a low level. Control unit 112 causes RO-pump 450 to start and run until the tank 350 is empty or almost empty. RO-pump 450 is then stopped and inlet valve 332 is opened. Inlet valve 332 is maintained open, and the second pump 316 is then run until a preset amount of chemical solution is metered into tank 350. When the level in tank 350 reaches a pre-determined level, the three-way valve 317 is opened to drain 339. RO-pump 450 circulates the fluid in the fluid circuit during the chemical intake phase and may be operated in two directions to create turbulent flow and to increase disinfection time and contact. At the end of the intake phase, reject bypass valve 321 is opened and the three-way valve 305*b* is actuated to open second drain path 388 to drain 339 and to drain the water level in tank 350 to a low level.

The described pre-treatment module 160, the RO module 170 and post-treatment module 180, are enclosed inside of a single integrated water purification cabinet 110*a*, except for the filter package 331, which is removably arranged, e.g. hinged, on the outside of the single water purification cabinet 110*a*. However, the water purification apparatus 110 is considered as being integrated in the sense that it is compact and built as one unit. The filter package 331 may then be exchanged when exhausted. In an alternative embodiment, the modules may be arranged in separate units. As mentioned above, purified water is sent from water purification apparatus 110 to disposable set 40 via water line 64. Referring to FIG. 1, water line 64 feeds purified water to a water port 282 of cassette 42 of disposable set 40. Water line 64 is in one embodiment a flexible tube having a first end connected to the water outlet connector 128 of the water purification apparatus 110 and a second end connected to a water port 282 of the cycler 20. Water line 64 may be at least 2 meters long and in one embodiment longer than 4 meters. Water line 64 allows water purification apparatus 110 to be installed in a room having an available water source, while cycler 20 resides in a different room in which the patient resides, e.g., sleeps. Water line 64 may accordingly be as long as necessary to connect water purification apparatus 110 to cycler 20.

FIG. 6 also illustrates that the disposable line set 40 includes a drain line 56 configuration arranged to conduct fluid, such as used dialysis fluid, to the drain 339 of the water purification apparatus 110. Drain line 56 is e.g. a tube having a first end connected to cassette 42 of cycler 20 and a second end including a drain line connector 58 (FIG. 1) connected to a drain connector 118 of the water purification apparatus 110. Drain line 56 may alternatively be a flexible tube, which may be more than 2 meters long and in some embodiments longer than 4 meters. Drain line 56 may be as long as necessary to connect between water purification apparatus 110 and cycler 20. Water line 64 and drain line 56 in the illustrated embodiment run parallel using dual lumen tubing. It is also possible that water purification apparatus 110 and cycler 20 are positioned close together, such that the same two line fluid path including water line 64 and drain line 56 may for example be less than 0.5 meters. Moreover, while a dual lumen water line 64 and the drain line 56 are illustrated, it is possible that water line 64 and drain line 56 are separate. A water tray 420 is positioned below the water purification apparatus 110. A liquid sensor 370 is arranged at the bottom of the water tray 420 to detect any leakage from the water purification apparatus 110. In one example embodiment, the water tray 420 is enclosed inside the purification cabinet 110a of the water purification apparatus 110.

Heat Disinfection

As described, the fluid circuit 404 includes the heating device 302 arranged to heat purified water from the RO device 301. The heating device 302 may heat the water to a suitable disinfection temperature above 65° C., for example between 80° C. and 95° C. The water may be heated to such a temperature directly by having a powerful heating device 302. Alternatively, the water may be gradually heated, recirculated to the tank 350, pumped by the RO-pump 450 through the membrane 324 and again heated by the heating device 302. The water purifying apparatus 110 is further arranged to heat disinfect the fluid circuit 404 using the heated purified water. The heated water is then circulated in the fluid circuit 404. The fluid circuit 404 may include the drain connector 118 and the water outlet connector 128. The water purifying apparatus 110 may then be arranged to heat disinfect the drain connector 118 and the water outlet connector 128 using the heated purified water. A door (not shown) is closed over the drain connector 118 and the water outlet connector 128 from the outside of the water purifying apparatus 110. When a contact sensor 345 (FIG. 6) such as a Hall sensor, detects that the door is closed, disinfection of the fluid circuit 404 and/or the connectors 118, 128 may be performed. Heated water is passed via the connectors 118, 128 and between the connectors 118, 128 via an internal bypass line 401a, such that the inside and the outside of the connectors 118, 128 are disinfected in the same disinfection run.

In an example embodiment, the control unit 112 of the water purifying apparatus 110 is programmed to periodically instruct the water purifying apparatus 110 to heat the purified water flowing in the fluid circuit 404 by means of the heating device 302 to a temperature above 65° C. and to control heat disinfection of the fluid circuit 404 using the heated water such that a certain disinfection criterion is met. The control unit 112 may initiate the heat disinfection automatically, or by instructions/commands from the cycler 20. The disinfection may also be initiated manually by the user. The disinfection criterion may include that the fluid circuit should be heat disinfected for a certain time with a certain temperature of the heated water. The time and temperature may for example be determined according to the well known A0 concept. The A0 concept is defined as:

$$A_0 = \Sigma 10^{(T-80)/z} \cdot \Delta t \quad (1)$$

z is a value defined by the type of microorganisms that need to be killed. For bacterial spores, which is the most resistant of all microorganisms, a z-value of z=10° is considered needed. At a temperature T of 80° C., the A0 expresses the time, $\Delta t$ is seconds, needed to reach an expected effect. If T=90° C., only a tenth of the time is needed, i.e. 6 seconds, to get an A0 of 60. If T instead is 70° C., the time needed is tenfold. An A0 value of 600 should be sufficient for disinfection when one patient is considered. However, an A0 value of 1000, or more, may also be considered. All temperatures above 65° C. are considered to have a disinfection effect and should be included in the calculation of A0. The water may thus be heated to a temperature above 65° C., for example between 85° C. and 95° C., and thus below boiling.

The connectors 118, 128 are typically disinfected each time the line set 40 has been disconnected from the connectors 118, 128, and the door (not shown) has been closed. The whole fluid circuit 404, including the RO membrane, the recirculation loops 381, 375, optionally the EDI 306, is disinfected 2 to 3 times each week, e.g. every second day. The whole fluid circuit 404 may include all circuit elements in the water purification apparatus 110 except the pretreatment circuit 402.

In an alternative embodiment, the line set 40 is not changed after each treatment. Instead, the line set 40 is re-used two, three or four times before it is exchanged. The line set 40 will then remain connected to the water purification apparatus 110. The line set 40 has to be disinfected after every treatment, and in one exemplary embodiment the control unit 112 is programmed to instruct the water purifying apparatus 110 to heat water flowing in the fluid circuit 404 by means of the heating device 302 and to output the heated water through the purified water outlet connector 128 to the line set 40 for heat disinfection of the line set 40. The heated water is then collected in the accumulator bag 66, and pumped to the mixing container 62 by means of the pump actuator 5 of the cycler 20, which is included in the instructions of the control unit 22 of the cycler 20. The control unit 22 of the cycler 20 may also comprise instructions for performing a heat disinfection of the line set 40. The instructions include to cause (i) the pump actuator 5 to pull heated water from the mixing container 62 into the pump chamber 44, cause (ii) the pump actuator 5 to operate the pump chamber 44 to push the hot water into the mixing container 62, and repeat (i) and (ii) at least one time. Thereby the heated water will flow in and out of the mixing container 62 to thoroughly heat disinfect the same. In one embodiment, the heat disinfection of the line set 40 should meet the same kind of disinfection criterion as of the fluid circuit 404 of the water purification apparatus 110, for example defined according to the A0 concept.

Figure 7:
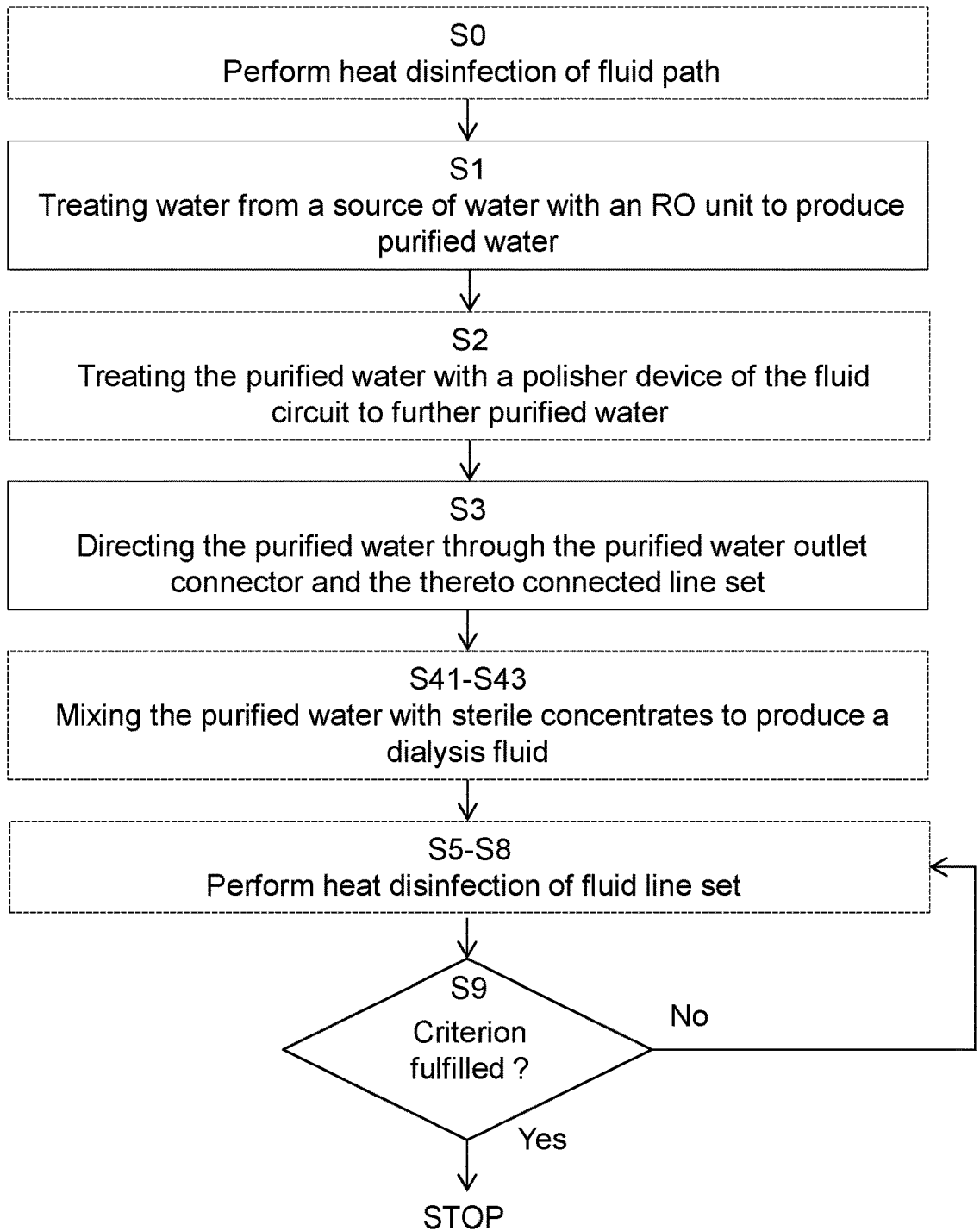
FIG. 7 illustrates a flow chart of a method for producing microbiologically controlled fluid according to some embodiments.

In the following a method for producing microbiologically controlled fluid with a system, for example the previously described system, will be explained with reference to the flowchart of FIG. 7. The system comprises a water purifying apparatus 110 with a heat disinfected fluid circuit 404 arranged for producing purified water, and a line set 40 connected to a water outlet connector 128 of the water purifying apparatus 110 for transporting the purified water to a point of use. The method may be implemented by a computer program comprising instructions which, when the program is executed by one or both of the described control units, cause one or both of the control units and the system as has been described to carry out the method according to any of the embodiments as described herein. The method may reside in a computer-readable medium. The computer-readable medium comprises instructions which, when executed by one or both of the control units, cause the one or both of the control units and the system to carry out the method according to any of the embodiments as described herein.

It is here presumed that the fluid circuit of the water purification apparatus has already been heat disinfected. Otherwise, the method may be initiated by performing S0 a heat disinfection of the fluid circuit 404, optionally including the connectors 118, 128. If the line set 40 is connected to the connectors 118, 128, the line set 40 may as well be heat disinfected. After the heat disinfection, and if the line set 40 was not connected, the user connects the line set 40 to the connectors 118, 128. Thereafter the water purification apparatus is ready to start producing purified water. The method comprises treating S1 water from a water source 398 with a RO unit 301 of the fluid circuit 404 to produce purified water from the RO unit 301, thus permeate water. The pre-filtered water is thus pushed through the membrane 324 of the RO unit 301, by means of the RO pump 450. In one exemplary embodiment, the method further comprises treating S2 the permeate water with a polisher device of the fluid circuit. The polisher device is for example an EDI device. The permeate water is pushed through the EDI by means of the RO pump 450. The produced purified water has an amount of bacteria that is less than 100 CFU/mL and an amount of bacterial endotoxins that is less than 0.25 EU/mL. If a polisher device is used, the polisher device may be capable of assisting in reducing, or further reducing, the amount of bacteria and endotoxins. In a further step, the method comprises directing S3 the purified water through the purified water outlet connector and the thereto connected line set 40 including at least one sterile sterilizing grade filter 70a, 70b, to produce sterile purified water with an amount of bacteria that is zero CFU/mL and an amount of bacterial endotoxins that is less than 0.05 EU/mL. This is achieved by providing the membrane of the filter/filters with certain characteristics such as a pore size less than one micrometer and a high molecular weight additive bearing cationic charges. The line set 40 accumulates the purified water in the accumulator bag 66.

In an exemplary embodiment, the line set 40 is arranged to operate with a pumping actuator 5 of a cycler 20. At least one concentrate source 84a, 84b is further connected to the line set 40. The method may then comprise causing S41 the pump actuator 5 of the cycler 20 to operate the pump chamber 20 of the line set 40 to pump a first amount of the purified water, from the accumulator bag 66, to a mixing container of the line set 40. To mix the purified water with concentrates, the method comprises causing S42 the pump actuator 5 to operate the pump chamber 20 to pump a prescribed amount of at least one concentrate from at least one concentrate source 84a, 84b to the mixing container 62. In one example embodiment, the method further comprises causing S43 the pump actuator 5 to operate the pump chamber 20 to pump a second amount of the purified water to the mixing container 62. The fluid may then be mixed by sequentially pumping in and out some fluid from the mixing container 62. The ready-mixed PD fluid is then ready to be infused into the patient P. By means of the pump actuator 5, the PD-fluid is infused into the patient P.

The disposable set including the one or more sterile sterilizing grade filter is discarded after each use in one embodiment. In alternative embodiments, the disposable set including the cassette, associated lines, heater/mixing bag, water accumulator (if provided) and one or more sterile sterilizing grade filter are reused for one or more additional treatment. To do so, it is contemplated to flush the disposable cassette with purified water at the end of treatment to push residual used dialysis fluid from the cassette and the drain line to drain. The patient disconnects the patient line from the patient's transfer set (which leads to the patient's indwelling peritoneal catheter) and caps the transfer set and patient line each with a cap, e.g., a cap containing a disinfectant. In an alternative embodiment, the drain line, for example, is provided with a port for connecting to the end of the patient line between treatments to create a patient line loop that may be more effectively flushed or disinfected. The concentrate lines of the cassette are left connected to the concentrate containers. The water line from the cassette is left connected to the water purifier. The drain line from the cassette is left connected to drain, e.g., via a drain line connection to the water purifier having the at least one conductivity sensor as discussed herein.

The line set 40 may now be disinfected such that it can be used again. In one exemplary embodiment, the method comprises heating S5 the produced purified water to a temperature above 65° C., directing S6 the heated purified water through the water outlet connector 128 and circulating S7 the heated purified water in the line set 40, in order to heat disinfect the line set 40. The method may additionally comprise to heat disinfect the fluid circuit 404 as has been previously described, including the RO membrane, in the same run or during the same disinfection cycle. The heated water is delivered to the water accumulator 66 in one embodiment. The cycler 20 in its last step at the end of treatment pulls heated purified water from the water accumulator 66 and pumps the water into and through the cassette, drain line and possibly even the heater/mixing container.

In an embodiment, control unit 22 of cycler 20 is programmed to cause cycler 20 to push and pull the heated water repeatedly throughout cassette 42 and heater/mixing bag 62, and repeatedly through water line segments 64a and 64b. The hot water is also cycled through drain line 56 and patient line 50, e.g., up to a hydrophobic membrane located in patient line connector 52. The heat disinfection of the fluid line set 40 may be continued until a certain disinfection criterion is met S9. If the criterion is fulfilled, the heat disinfection of the line set is stopped and the heated water directed to drain. If the criterion is not fulfilled, the heat disinfection is continued. The criterion may include that the hot water should be circulated for a certain time with a certain temperature. For example, the temperature should be between 85° C. and 95° C., and the time between 0.5 and 2 hours. The time and temperature may be determined according to the A0 concept, as known in the art. When the hot water disinfection of semi-disposable set 40 is completed, the hot water is sent to drain 339 at the water purification apparatus 110.

In an embodiment, a supply of the bacterial growth prevention agent is connected as an input to the water purification apparatus 110. The water purification apparatus 110 as a last step at the end of treatment mixes a desired amount of the bacterial growth prevention agent into the purified water, which is then delivered to the water accumulator 66 in one embodiment. The water may also be heated by the heating device in the water purification device 110 to a high temperature as has been previously described. The cycler 20 in its last step at the end of treatment pulls purified water including the growth inhibitor from the water accumulator 66 and pumps the water and inhibitor into and through the cassette, drain line and possibly even the heater/mixing container, that is, performs the same procedure as has been described in connection with disinfection with heated purified water only. After the disinfection is finished, the used water is passed to drain 339.

In an embodiment, the number of times that the disposable set may be reused is keyed off of the level of concentrates in the concentrate containers. For example, the concentrate containers may be configured to hold and provide three treatment's worth of concentrate (plus some extra to ensure three full treatments). It is therefore intended that the disposable set be reused two times, so that at the end of three treatments, the patient may simply remove the disposable set with concentrate containers connected from the cycler for disposal, and reconnect a new disposable set along with two new concentrate containers. It is contemplated that the control unit of the cycler keep track of the amount of each concentrate consumed over the three treatment period so that the control unit may (i) prevent the user from beginning a treatment when there is not enough of either concentrate to complete the treatment and/or (ii) provide an option to the user to perform a treatment with one or more less cycles.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the scope of the appended claims.

The invention claimed is:

1. A system comprising:
a line set connected to a purified water outlet connector, wherein the line set includes at least one sterilizing filter; and
a water purifying apparatus fluidly connected with the line set, the water purifying apparatus including
(i) a pre-filter circuit connected to a water inlet for receiving water from a water source, wherein the pre-filter circuit includes a particle filter and an activated carbon filter, wherein each of the particle filter and the activated carbon filter are arranged to filter water received via the water inlet to produce pre-treated water,
(ii) a fluid circuit arranged to receive pre-treated water from the pre-filter circuit and to produce purified water, wherein the fluid circuit includes
a pump,
a reverse osmosis device, and
a heating device arranged to heat purified water output from the reverse osmosis device to a temperature above 65° C., and
(iii) the purified water outlet connector, wherein the water purifying apparatus is configured to
pump pre-treated water through the reverse osmosis device using the pump,
produce purified water using the reverse osmosis device,
disinfect the fluid circuit using the heated purified water output from the heating device, and
after heat disinfection is completed, output purified water through the purified water outlet connector,
wherein the at least one sterilizing filter of the line set is arranged to further filter the purified water.

2. The system according to claim 1, wherein the line set is a reusable line set.

3. The system according to claim 1, wherein the fluid circuit is arranged to produce purified water having an amount of bacteria that is less than 100 Colony-Forming Units/mL and an amount of bacterial endotoxins that is less than 0.25 Endotoxin Units/mL.

4. The system according to claim 1, wherein the at least one sterilizing filter is arranged to further filter the purified water into sterile purified water having an amount of bacteria that is zero Colony-Forming Units/mL and an amount of bacterial endotoxins that is less than 0.05 Endotoxin Units/mL.

5. The system according to claim 1, wherein the fluid circuit further includes a polisher device arranged to treat the purified water from the reverse osmosis device and output further purified water, wherein the fluid circuit is arranged to output the further purified water through the water outlet connector.

6. The system according to claim 1, wherein the line set further includes a drain line connected at a drain line connector of the drain line to a drain connector of the water purifying apparatus, wherein the water purifying apparatus further includes a first drain path connected to the drain connector for transporting drain fluid received from the drain line to a drain.

7. The system according to claim 6, wherein the water purifying apparatus is arranged to disinfect the drain connector and the water outlet connector of the water purifying apparatus using the heated purified water.

8. The system according to claim 1, wherein the water purifying apparatus includes a control unit programmed to
periodically instruct the water purifying apparatus to heat the purified water flowing in the fluid circuit by means of the heating device to a temperature above 65° C.; and
control heat disinfection of the fluid circuit using the heated water such that a certain disinfection criterion is met.

9. The system according to claim 8, wherein the control unit is programmed to instruct the water purifying apparatus to heat purified water flowing in the fluid circuit by means of the heating device and to output the heated purified water through the purified water outlet connector to the line set for heat disinfection of the line set.

10. The system according to claim 1, further comprising at least one concentrate source; and
a cycler including
a control unit,
a pump actuator arranged to be controlled by the control unit, wherein the line set is operable with the cycler, and wherein the line set further includes
a pumping cassette including a pump chamber configured to be actuated by the pump actuator, and
a mixing container in fluid communication with the pumping cassette, and
a memory storing instructions, which when executed by the control unit, cause the control unit to
cause the pump actuator to operate the pump chamber to pump a first amount of the purified water to the mixing container, and
cause the pump actuator to operate the pump chamber to pump a prescribed amount of the at least one concentrate from the at least one concentrate source to the mixing container.

11. The system according to claim 10, wherein the instructions further cause the control unit to cause the pump actuator to circulate heated purified water in the line set to perform heat disinfection of the line set.

12. A method for producing microbiologically controlled fluid using a system comprising a water purifying apparatus including a heat disinfected fluid circuit arranged for producing purified water and a line set connected to a purified water outlet connector of the water purifying apparatus for transporting the purified water to a point of use, wherein the method comprises:
treating water from a water source with a reverse osmosis unit of the fluid circuit to produce purified water, wherein the purified water includes an amount of bacteria that is less than 100 Colony-Forming Units/ mL and an amount of bacterial endotoxins that is less than 0.25 Endotoxin Units/mL; and directing the purified water through the purified water outlet connector and through the connected line set to produce sterile purified water, wherein the connected line set includes at least one sterilizing filter, and wherein the sterile purified water includes an amount of bacteria that is zero Colony-Forming Units/mL and an amount of bacterial endotoxins that is less than 0.05 Endotoxins Units/mL.

13. The method according to claim 12, further comprising treating the water from the water source with a particle filter and an activated carbon filter prior to treating the water with the reverse osmosis unit.

14. The method according to claim 12, wherein the system further comprises a cycler, and the method further comprises:

causing a pump actuator of the cycler to operate a pump chamber of the line set to pump a first amount of the purified water to a mixing container of the line set; and causing the pump actuator to operate the pump chamber to pump a prescribed amount of at least one concentrate from at least one concentrate source to the mixing container.

15. The method according to claim 12, further comprising:

heating the produced purified water to a temperature above 65° C.;

directing the heated purified water through the purified water outlet connector; and circulating the heated purified water in the line set to perform heat disinfection of the line set.

16. The method according to claim 12, comprising treating purified water from the reverse osmosis unit with a polisher device.

17. A water purifying apparatus comprising:
a pump;
a fluid circuit including a purified water outlet connector;
a reverse osmosis device;
a heating device; and
a non-transitory, computer-readable medium storing instructions which, when performed by a processor, cause the processor to:
cause the pump to pump pre-treated water in the fluid circuit through the reverse osmosis device to produce purified water;
periodically instruct the heating device to heat purified water flowing in the fluid circuit to a temperature above 65° C.;
control heat disinfection of the fluid circuit using the heated purified water such that a certain disinfection criterion is met; and
after heat disinfection is completed, cause the pump to pump purified water through the purified water outlet connector to a line set including at least one sterilizing filter.

18. The water purifying apparatus of claim 17, wherein the instructions further cause the processor to:
cause a pump actuator of a cycler to operate a pump chamber of the line set to pump a first amount of the purified water to a mixing container of the line set; and
cause the pump actuator to operate the pump chamber to pump a prescribed amount of at least one concentrate from at least one concentrate source to the mixing container.

19. The purifying apparatus of claim 18, wherein the instructions further cause the processor to cause the pump actuator of the cycler to circulate heated purified water in the line set to perform heat disinfection of the line set.

20. The water purifying apparatus of claim 17, which further includes a polisher device in the fluid circuit, and wherein the instructions further cause the processor to cause the pump to pump purified water from the reverse osmosis device through the polisher device.

* * * * *